United States Patent
Brangwynne et al.

(10) Patent No.: US 10,533,167 B2
(45) Date of Patent: Jan. 14, 2020

(54) OPTOGENETIC TOOL FOR RAPID AND REVERSIBLE CLUSTERING OF PROTEINS

(71) Applicant: The Trustees of Princeton University, Princeton, NJ (US)

(72) Inventors: Cliff Brangwynne, Hopewell, NJ (US); Jared Toettcher, Princeton, NJ (US); Yongdae Shin, Lawrenceville, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 0 days.

(21) Appl. No.: 15/618,345

(22) Filed: Jun. 9, 2017

(65) Prior Publication Data
US 2017/0355977 A1    Dec. 14, 2017

Related U.S. Application Data

(60) Provisional application No. 62/347,677, filed on Jun. 9, 2016, provisional application No. 62/362,889, filed on Jul. 15, 2016, provisional application No. 62/424,924, filed on Nov. 21, 2016.

(51) Int. Cl.
*C12N 9/88* (2006.01)
*C07K 14/435* (2006.01)
*C12N 13/00* (2006.01)

(52) U.S. Cl.
CPC .......... *C12N 9/88* (2013.01); *C07K 14/43595* (2013.01); *C12N 13/00* (2013.01); *C12Y 401/99003* (2013.01); *C07K 2319/60* (2013.01); *C07K 2319/70* (2013.01)

(58) Field of Classification Search
CPC .......... C12N 9/88; C12N 13/00; C07K 14/47; C07K 1/36
See application file for complete search history.

(56) References Cited

PUBLICATIONS

Thieulin-Pardo et al. May 19, 2015; Fairy "tails": flexibility and function of intrinsically disordered extension in the photosynthetic world. Frontiers in Molecular Biosciences. vol. 2, Article 23, pp. 1-18.*
Kedersha, N.L , Gupta, M., Li, W., Miller, I. , and Anderson, P. "RNA-binding proteins TIA-1 and TIAR link the phosphorylation of eIF-2a to the Assembly of Mammalian Stress Granules." J. Cell Biol. 147, 1431-1441, 1999.
Kroschwald, S. , Maharana, S., Mateju, D., Malinovska, L., Nüske, E. , Poser, I., Richter, D., and Alberti, S. Promiscuous interactions and protein disaggregases determine the material state of stress-inducible RNP granules. Elife 4, e06807, 2015.
Langer, J.S., and Schwartz, A.J. "Kinetics of nucleation in near-critical fluids." Phys. Rev. A 21, 948-958, 1980.
Lee, C.F., Brangwynne, C.P., Gharakhani, J., Hyman, A a., and Jülicher, F. "Spatial organization of the cell cytoplasm by position-dependent phase separation." Phys. Rev. Lett. 111,88101, 2013.
Lu, P.J., Zaccarelli, E., Ciulla, F., Schofield, A.B., Sciortino, F., and Weitz, D.A "Gelation of particles with short-range attraction." Nature 453, 499-503, 2008.
Mollet, S., Cougot, N., Wilczynska, A., Dautry, F., Kress, M., Bertrand, E., and Weil, D. "Translationally repressed mRNA transiently cycles through stress granules during stress." Mol. Biol. Cell 19, 4469-4479, 2008.
Murakami, T. , Qamar, S., Lin, J.Q., Schierle, G.S.K. , Rees, E., Miyashita, A , Costa, A.R., Dodd. R.B., Chan, F.T.S., Michel. C.H., et al. "ALS/FTD Mutation-Induced Phase Transition of FUS Liquid Droplets and Reversible Hydrogels into Irreversible Hydrogels Impairs RNP Granule Function." Neuron 678-690, 2015.
Muschol, M., and Rosenberger, F. "Liquid-Liquid Phase Separation in Supersaturated Lysozyme Solutions and Associated Precipitate Formation/Crystallization." J. Chern. Phys. 107, 1953-1962, 1997.
Plakoutsi, G., Bemporad, F., Calamai, M., Taddei, N., Dobson, C.M., and Chiti, F. "Evidence for a mechanism of amyloid formation involving molecular reorganisation within native-like precursor aggregates." J. Mol Biol. 351, 910-922, 2005.
Sagui, C., and Grant, M. "Theory of nucleation and growth during phase separation." Phys. Rev. E 59, 4175-4187, 1999.
Schwartz, J.C., Cech, T.R. , and Parker, RR. "Biochemical Properties and Biological Functions of FET Proteins." Annu. Rev. Biochem. 84, 355-379, 2015.
Tischer, D., and Weiner, O.D. "Illuminating cell signalling with optogenetic tools." Nat Rev Mol Cell Biol 15, 551-558, 2014.
Tourriére, H., Chebli, K. , Zekri, L., Courselaud, B., Blanchard, J.M., Bertrand, E. , and Tazi, J. "The RasGAP-associated endoribonuclease G38P assembles stress granules." J. Cell Biol. 160, 823-831, 2003.
Voorhees, P.W. "Ostwald ripening of Two-Phase Mixtures." Annu. Rev. Mater. Sci. 22, 197-215, 1992.
Mao et al. "Biogenesis and function of nuclear bodies", Trends in Genetics, vol. 27, No. 8, Aug. 2011.

(Continued)

*Primary Examiner* — Karen Cochrane Carlson
(74) *Attorney, Agent, or Firm* — Meagher Emanuel Laks Goldberg & Liao, LLP

(57) ABSTRACT

A protein construct including a gene encoding a light-sensitive protein fused to at least one of either a low complexity sequence, an intrinsically disordered protein region (IDR), or a repeating sequence of a linker and another gene encoding a light-sensitive protein. Among the many different possibilities contemplated, the protein construct may also advantageously include cleavage tags. This protein construct may be utilized for a variety of functions, including a method for protein purification, which requires introducing the protein construct into a living cell, and inducing the formation of clusters by irradiating the construct with light. The method may also advantageously include cleaving a target protein from an IDR, and separating the clusters via centrifuge. A kit for practicing in vivo aggregation or liquid-liquid phase separation is also included, the kit including the protein construct and a light source capable of producing a wavelength that the light-sensitive protein will respond to.

20 Claims, 13 Drawing Sheets
Specification includes a Sequence Listing.

(56) References Cited

PUBLICATIONS

Anderson et al. "RNA granules: post-transcriptional and epigenetic modulators of gene expression" Nature reviews Molecular cell biology, vol. 10, No. 6, pp. 430-436, Jun. 2009.

Buchan et al. "Eukaryotic Stress Granules: The Ins and Outs of Translation", Molecular Cell. 36(6):932-41, Dec. 24, 2009.

Handwerger et al. "Subnuclear organelles: new insights into form and function", Trends in Cell Biology, vol. 16, No. 1, Jan. 2006.

Li et al. "Stress granules as crucibles of ALS pathogenesis", The Journal of Cell Biology, 201 (3): 361, Apr. 29, 2013.

Ramaswami et al. "Altered Ribostasis: RNA-Protein Granules in Degenerative Disorders", Cell 154, pp. 727-736, Aug. 15, 2013.

Phair et al. "High mobility of proteins in the mammalian cell nucleus", Nature, vol. 404, pp. 604-609, Apr. 6, 2000.

Brangwynne et al. "Germline P Granlues Are Liquid Droplets That Localize by Controlled Dissolution/Condensation" Science, vol. 324, pp. 1729-1733, Jun. 26, 2009.

Brangwynne et al. "Active liquid-like behavior of nucleoli determines their size and shape in Xenopus Iaevis oocytes", Proc Natl Acad Sci U S A. 108(11):4334-9, Mar. 15, 2011.

Feric et al. "A nuclear F-actin scaffold stabilizes ribonucleoprotein droplets against gravity in large cells", Nature Cell Biology, vol. 15, No. 10, Oct. 2013.

Ishimoto et al. "Critical Behavior of a Binary Mixture of Protein and Salt Water", Physical Review Letters, vol. 39, No. 8, pp. 474-477, Aug. 22, 1977.

Peter G. Vekilov "Phase transitions of folded proteins", The Royal Society of Chemistry, Soft Matter, 6, 5254-5272, Jun. 30, 2010.

Weber et al. "Inverse Size Scaling of the Nucleolus by a Concentration-Dependent Phase Transition", Current Biology 25, 641-846, Mar. 2, 2015.

Nott et al. "Phase Transition of a Disordered Nuage Protein Generates Environmentally Responsive Membraneless Organelles", Molecular Cell 57, 936-947, Mar. 5, 2015.

Wippich et al. "Dual Specificity Kinase DYRK3 Couples Stress Granule Condensation/Dissolution to mTORC1 Signaling", Cell 152, 791-805, Feb. 14, 2013.

Molliex et al. "Phase Separation by Low Complexity Domains Promotes Stress Granule Assembly and Drives Pathological Fibrillization", Cell 163, 123-133, Sep. 24, 2015.

Li et al. "Phase transitions in the assembly of multivalent signalling proteins", Nature, vol. 483, pp. 336-341, Mar. 15, 2012.

Sudeep Banjade Michael K Rosen: "Phase transitions of multivalent proteins can promote clustering of membrane receptors", Biophysics and Structural Biology Cell Biology, eLife 2014;3:e04123, Oct. 16, 2014.

Elbaum-Gartinkle et al. "The disordered P granule protein LAF-1 drives phase separation into droplets with tunable viscosity and dynamics", PNAS, vol. 112, No. 23, pp. 7189-7194, Jun. 9, 2015.

Lin et al. "Formation and Maturation of Phase-Separated Liquid Droplets by RNA-Binding Proteins", Molecular Cell 60, pp. 208-219, Oct. 15, 2015.

Zhang et al. "RNA Controls PolyQ Protein Phase Transitions", Molecular Cell 60, 220-230, Oct. 15, 2015.

Weber et al. "Getting RNA and Protein in Phase", Cell 149, pp. 1188-1191, Jun. 8, 2012.

Xiang et al. "The LC Domain of hnRNPA2 Adopts Similar Conformations in Hydrogel Polymers, Liquid-like Droplets, and Nuclei", Cell 163, 829-839, Nov. 5, 2015.

Patel et al. "A Liquid-to-Solid Phase Transition of the ALS Protein FUS Accelerated by Disease Mutation", Cell 162, 1066-1077, Aug. 27, 2015.

Toettcher et al. "Light-based feedback for controlling intracellular signaling dynamics", Nature Methods, vol. 8, No. 10, pp. 837-841, Oct. 2011.

Kennedy et al. "Rapid blue-light—mediated induction of protein interactions in living cells", Nature Methods, vol. 7, No. 12, pp. 973-841, Dec. 2010.

Levskaya et al. "Spatiotemporal control of cell signalling using a light-switchable protein interaction", Nature, vol. 461, pp. 997-1001, Oct. 15, 2009.

Bugaj et al. "Optogenetic protein clustering and signaling activation in mammalian cells", Nature Methods, vol. 10, No. 3, pp. 249-254, Mar. 2013.

Lee et al. "Reversible protein inactivation by optogenetic trapping in cells", Nature Methods, vol. 11, No. 6, pp. 533-638, Jun. 2014.

Taslimi et al. "An optimized optogenetic clustering tool for probing protein interaction and function", Nature Communications | DOI: 10.1038/ncomms5925, 2014.

Kato, M., Han, T.W. , Xie, S., Shi, K. , Du, X., Wu, L.C., Mirzaei, H., Goldsmith, E.J., Longgood, J., Pei, J., et al. "Cell-free formation of RNA granules: Low complexity sequence domains form dynamic fibers within hydrogels." Cell 149, 753-767, 2012.

Y. Shin et al. "Spatiotemporal Control of Intracellular Phase Transitions Using Light-Activated optoDroplets" Cell. 168 (1-2); Jan. 12, 2017 Filed under previous title: "Optogenetic FUS droplets reveal intracellular transition from reversible gels to persistent aggregates".

S. F. Banani et al., "Compositional Control of Phase-Separated Cellular Bodies." Cell, 2016.

L. Li, J. O. Fierer, T. A. Rapoport, M. Howarth, "Structural analysis and optimization of the covalent association between SpyCatcher and a peptide Tag." Journal of molecular biology 426, 309-317 (2014).

Wu, Y.I., Frey, D., Lungu, O.I. , Jaehrig, A , Schlichting, I. , and Hahn, K.M. "A genetically-encoded photoactivatable Rae controls the mobility of living cells." Nature 461, 104-108; 2009.

Zaccarelli, E. "Colloidal Gels: Equilibrium and Non-Equilibrium Routes." J. Phys. Condens. Matter 19, 323101, 2007.

Zwicker, D., Decker, M., Jaensch, S., Hyman, A a, and Jülicher, F. "Centrosomes are autocatalytic droplets of pericentriolar material organized by centrioles." Proc. Natl. Acad. Sci. U. S. A 111, E2636-E2645, 2014.

Banerjee R., Schleicher, E., Meier, S. , Viana, R.M., Pokorny, R., Ahmad, M., Bittl, R., and Batschauer, A "The signaling state of Arabidopsis cryptochrome 2 contains flavin semiquinone." J. Biol. Chem. 282, 14916-14922, 2007.

Berry, J., Weber, S.C., Vaidya, N., Haataja, M., and Brangwynne, C.P. "RNA transcription modulates phase transition-driven nuclear body assembly." Proc. Natl. Acad. Sci. U. S. A. 112, E5237-E5245. 2015.

Bucciantini, M., Giannoni, E. , Chiti, F. , Baroni, F., Formigli, L. , Zurdo, J. , Taddei, N., Ramponi, G., Dobson, C.M., and Stefani, M. "Inherent toxicity of aggregates implies a common mechanism for protein misfolding diseases." Nature 416, 507- 511; 2002.

Burke, K. a, Janke, AM., Rhine, C.L., and Fawzi, N.L. "Residue-by-Residue View of In Vitro FUS Granules that Bind the C-Terminal Domain of RNA Polymerase II." Mol. Cell 60, 231-241; 2015.

Cardinaux, F. , Gibaud, T., Stradner, A, and Schurtenberger, P. "Interplay between spinodal decomposition and glass formation in proteins exhibiting short-range attractions." Phys. Rev. Lett. 99, 118301, 2007.

Chiti, F., and Dobson, C.M. "Amyloid formation by globular proteins under native conditions." Nat Chem. Biol. 5, 15-22, 2009.

Dormann, D., and Haass, C. "Fused in sarcoma (FUS): An oncogene goes awry in neurodegeneration." Mol. Cell. Neurosci. 56, 475-486, 2013.

Dumetz, AC., Chockla, AM. , Kaler, E.W., and Lenhoff, AM. "Protein Phase Behavior in Aqueous Solutions: Crystallization, Liquid-Liquid Phase Separation, Gels, and Aggregates." Biophys. J. 94, 570-583, 2008.

Feric, M., Vaidya, N., Harmon, T.S., Mitrea, D.M., Zhu, L. , Richardson, T.M .. Kriwacki, R.W., Pappu, R. V. , and Brangwynne, C.P. "Coexisting liquid phases underlie nucleolar sub-compartments." Cell 165, 1686-1697, 2016.

Van Genuchten, M.T., and Alves, W.J. "Analytical Solutions of tile One-Dimensional Convective-Dispersive Solute Transport Equation." Tech. Bull. United States Dep. Agric. Econ. Res. Serv. 157268, 1982.

Guil, S., Long, J.C., and Cáceres, J.F. "hnRNP A1 relocalization to the stress granules reflects a role in the stress response." Mol. Cell. Biol. 26, 57 44-5758, 2006.

(56) References Cited

PUBLICATIONS

Jain, S., Wheeler, J.R., Walters, R.W., Agrawal, A, Barsic, A, Parker, R., Jain, S., Wheeler, J.R., Walters, R.W., Agrawal, A, et al. ATPase-Modulated Stress Granules Contain a Diverse Proteome and Substructure. Cell 164, 487-498, 2016.

* cited by examiner

SEQUENCE LISTING

```
<160> NUMBER OF SEQ ID NOS: 5

<210> SEQ ID NO 1
<211> LENGTH: 19
<212> TYPE: PRT
<213> ORGANISM: Artificial Sequence
<220> FEATURE:
<223> OTHER INFORMATION: GCN4

<400> SEQUENCE: 1

Glu Glu Leu Leu Ser Lys Asn Tyr His Leu Glu Asn Glu Val Ala Arg
1               5                   10                  15

Leu Lys Lys

<210> SEQ ID NO 2
<211> LENGTH: 16
<212> TYPE: PRT
<213> ORGANISM: Artificial Sequence
<220> FEATURE:
<223> OTHER INFORMATION: GFP11

<400> SEQUENCE: 2

Arg Asp His Met Val Leu His Glu Tyr Val Asn Ala Ala Gly Ile Thr
1               5                   10                  15

<210> SEQ ID NO 3
<211> LENGTH: 526
<212> TYPE: PRT
<213> ORGANISM: Homo sapiens

<400> SEQUENCE: 3

Met Ala Ser Asn Asp Tyr Thr Gln Gln Ala Thr Gln Ser Tyr Gly Ala
1               5                   10                  15

Tyr Pro Thr Gln Pro Gly Gln Gly Tyr Ser Gln Gln Ser Ser Gln Pro
                20                  25                  30

Tyr Gly Gln Gln Ser Tyr Ser Gly Tyr Ser Gln Ser Thr Asp Thr Ser
            35                  40                  45

Gly Tyr Gly Gln Ser Ser Tyr Ser Ser Tyr Gly Gln Ser Gln Asn Thr
        50                  55                  60

Gly Tyr Gly Thr Gln Ser Thr Pro Gln Gly Tyr Gly Ser Thr Gly Gly
65                  70                  75                  80

Tyr Gly Ser Ser Gln Ser Ser Gln Ser Ser Tyr Gly Gln Gln Ser Ser
                85                  90                  95

Tyr Pro Gly Tyr Gly Gln Gln Pro Ala Pro Ser Ser Thr Ser Gly Ser
                100                 105                 110
```

-continued

```
Tyr Gly Ser Ser Ser Gln Ser Ser Tyr Gly Gln Pro Gln Ser Gly
        115                 120                 125
Ser Tyr Ser Gln Gln Pro Ser Tyr Gly Gly Gln Gln Ser Tyr Gly
        130                 135                 140
Gln Gln Gln Ser Tyr Asn Pro Pro Gln Gly Tyr Gly Gln Asn Gln
145                 150                 155                 160
Tyr Asn Ser Ser Gly Gly Gly Gly Gly Gly Gly Gly Gly Gly Asn
                165                 170                 175
Tyr Gly Gln Asp Gln Ser Ser Met Ser Ser Gly Gly Ser Gly Gly
        180                 185                 190
Gly Tyr Gly Asn Gln Asp Gln Ser Gly Gly Gly Ser Gly Gly Tyr
        195                 200                 205
Gly Gln Gln Asp Arg Gly Gly Arg Gly Arg Gly Gly Ser Gly Gly
        210                 215                 220
Gly Gly Gly Gly Gly Gly Tyr Asn Arg Ser Ser Gly Gly Tyr Glu
225                 230                 235                 240
Pro Arg Gly Arg Gly Gly Arg Gly Arg Gly Gly Met Gly Gly
                245                 250                 255
Ser Asp Arg Gly Gly Phe Asn Lys Phe Gly Gly Pro Arg Asp Gln Gly
        260                 265                 270
Ser Arg His Asp Ser Glu Gln Asp Asn Ser Asp Asn Asn Thr Ile Phe
        275                 280                 285
Val Gln Gly Leu Gly Glu Asn Val Thr Ile Glu Ser Val Ala Asp Tyr
        290                 295                 300
Phe Lys Gln Ile Gly Ile Ile Lys Thr Asn Lys Lys Thr Gly Gln Pro
305                 310                 315                 320
Met Ile Asn Leu Tyr Thr Asp Arg Glu Thr Gly Lys Leu Lys Gly Glu
                325                 330                 335
Ala Thr Val Ser Phe Asp Asp Pro Pro Ser Ala Lys Ala Ala Ile Asp
        340                 345                 350
Trp Phe Asp Gly Lys Glu Phe Ser Gly Asn Pro Ile Lys Val Ser Phe
        355                 360                 365
Ala Thr Arg Arg Ala Asp Phe Asn Arg Gly Gly Gly Asn Gly Arg Gly
        370                 375                 380
Gly Arg Gly Arg Gly Gly Pro Met Gly Arg Gly Gly Tyr Gly Gly Gly
385                 390                 395                 400
Gly Ser Gly Gly Gly Gly Arg Gly Gly Phe Pro Ser Gly Gly Gly Gly
                405                 410                 415
Gly Gly Gly Gln Gln Arg Ala Gly Asp Trp Lys Cys Pro Asn Pro Thr
        420                 425                 430
Cys Glu Asn Met Asn Phe Ser Trp Arg Asn Glu Cys Asn Gln Cys Lys
        435                 440                 445
Ala Pro Lys Pro Asp Gly Pro Gly Gly Pro Gly Gly Ser His Met
450                 455                 460
Gly Gly Asn Tyr Gly Asp Asp Arg Arg Gly Gly Arg Gly Gly Tyr Asp
465                 470                 475                 480
Arg Gly Gly Tyr Arg Gly Arg Gly Gly Asp Arg Gly Gly Phe Arg Gly
                485                 490                 495
Gly Arg Gly Gly Gly Asp Arg Gly Gly Phe Gly Pro Gly Lys Met Asp
                500                 505                 510
Ser Arg Gly Glu His Arg Gln Asp Arg Arg Glu Arg Pro Tyr
        515                 520                 525
```

<210> SEQ ID NO 4
<211> LENGTH: 724
<212> TYPE: PRT
<213> ORGANISM: Homo sapiens

<400> SEQUENCE: 4

```
Met Gly Asp Glu Asp Trp Glu Ala Glu Ile Asn Pro His Met Ser Ser
1               5                   10                  15

Tyr Val Pro Ile Phe Glu Lys Asp Arg Tyr Ser Gly Glu Asn Gly Asp
            20                  25                  30

Asn Phe Asn Arg Thr Pro Ala Ser Ser Glu Met Asp Asp Gly Pro
        35                  40                  45

Ser Arg Arg Asp His Phe Met Lys Ser Gly Phe Ala Ser Gly Arg Asn
    50                  55                  60

Phe Gly Asn Arg Asp Ala Gly Glu Cys Asn Lys Arg Asp Asn Thr Ser
65                  70                  75                  80

Thr Met Gly Gly Phe Gly Val Gly Lys Ser Phe Gly Asn Arg Gly Phe
                85                  90                  95

Ser Asn Ser Arg Phe Glu Asp Gly Asp Ser Ser Gly Phe Trp Arg Glu
            100                 105                 110

Ser Ser Asn Asp Cys Glu Asp Asn Pro Thr Arg Asn Arg Gly Phe Ser
        115                 120                 125

Lys Arg Gly Gly Tyr Arg Asp Gly Asn Asn Ser Glu Ala Ser Gly Pro
    130                 135                 140

Tyr Arg Arg Gly Gly Arg Gly Ser Phe Arg Gly Cys Arg Gly Gly Phe
145                 150                 155                 160

Gly Leu Gly Ser Pro Asn Asn Asp Leu Asp Pro Asp Glu Cys Met Gln
                165                 170                 175

Arg Thr Gly Gly Leu Phe Gly Ser Arg Arg Pro Val Leu Ser Gly Thr
            180                 185                 190

Gly Asn Gly Asp Thr Ser Gln Ser Arg Ser Gly Ser Gly Ser Glu Arg
        195                 200                 205

Gly Gly Tyr Lys Gly Leu Asn Glu Glu Val Ile Thr Gly Ser Gly Lys
    210                 215                 220

Asn Ser Trp Lys Ser Glu Ala Glu Gly Gly Glu Ser Ser Asp Thr Gln
225                 230                 235                 240

Gly Pro Lys Val Thr Tyr Ile Pro Pro Pro Pro Glu Asp Glu Asp
                245                 250                 255

Ser Ile Phe Ala His Tyr Gln Thr Gly Ile Asn Phe Asp Lys Tyr Asp
            260                 265                 270

Thr Ile Leu Val Glu Val Ser Gly His Asp Ala Pro Pro Ala Ile Leu
        275                 280                 285

Thr Phe Glu Glu Ala Asn Leu Cys Gln Thr Leu Asn Asn Asn Ile Ala
    290                 295                 300

Lys Ala Gly Tyr Thr Lys Leu Thr Pro Val Gln Lys Tyr Ser Ile Pro
305                 310                 315                 320

Ile Ile Leu Ala Gly Arg Asp Leu Met Ala Cys Ala Gln Thr Gly Ser
                325                 330                 335

Gly Lys Thr Ala Ala Phe Leu Leu Pro Ile Leu Ala His Met Met His
            340                 345                 350

Asp Gly Ile Thr Ala Ser Arg Phe Lys Glu Leu Gln Glu Pro Glu Cys
        355                 360                 365

Ile Ile Val Ala Pro Thr Arg Glu Leu Val Asn Gln Ile Tyr Leu Glu
    370                 375                 380
```

Ala Arg Lys Phe Ser Phe Gly Thr Cys Val Arg Ala Val Val Ile Tyr
385                 390                 395                 400

Gly Gly Thr Gln Leu Gly His Ser Ile Arg Gln Ile Val Gln Gly Cys
            405                 410                 415

Asn Ile Leu Cys Ala Thr Pro Gly Arg Leu Met Asp Ile Ile Gly Lys
        420                 425                 430

Glu Lys Ile Gly Leu Lys Gln Ile Lys Tyr Leu Val Leu Asp Glu Ala
            435                 440                 445

Asp Arg Met Leu Asp Met Gly Phe Gly Pro Glu Met Lys Lys Leu Ile
    450                 455                 460

Ser Cys Pro Gly Met Pro Ser Lys Glu Gln Arg Gln Thr Leu Met Phe
465                 470                 475                 480

Ser Ala Thr Phe Pro Glu Glu Ile Gln Arg Leu Ala Ala Glu Phe Leu
                485                 490                 495

Lys Ser Asn Tyr Leu Phe Val Ala Val Gly Gln Val Gly Gly Ala Cys
                500                 505                 510

Arg Asp Val Gln Gln Thr Val Leu Gln Val Gly Gln Phe Ser Lys Arg
            515                 520                 525

Glu Lys Leu Val Glu Ile Leu Arg Asn Ile Gly Asp Glu Arg Thr Met
530                 535                 540

Val Phe Val Glu Thr Lys Lys Lys Ala Asp Phe Ile Ala Thr Phe Leu
545                 550                 555                 560

Cys Gln Glu Lys Ile Ser Thr Thr Ser Ile His Gly Asp Arg Glu Gln
                565                 570                 575

Arg Glu Arg Glu Gln Ala Leu Gly Asp Phe Arg Phe Gly Lys Cys Pro
            580                 585                 590

Val Leu Val Ala Thr Ser Val Ala Ala Arg Gly Leu Asp Ile Glu Asn
            595                 600                 605

Val Gln His Val Ile Asn Phe Asp Leu Pro Ser Thr Ile Asp Glu Tyr
        610                 615                 620

Val His Arg Ile Gly Arg Thr Gly Arg Cys Gly Asn Thr Gly Arg Ala
625                 630                 635                 640

Ile Ser Phe Phe Asp Leu Glu Ser Asp Asn His Leu Ala Gln Pro Leu
                645                 650                 655

Val Lys Val Leu Thr Asp Ala Gln Gln Asp Val Pro Ala Trp Leu Glu
                660                 665                 670

Glu Ile Ala Phe Ser Thr Tyr Ile Pro Gly Phe Ser Gly Ser Thr Arg
            675                 680                 685

Gly Asn Val Phe Ala Ser Val Asp Thr Arg Lys Gly Lys Ser Thr Leu
        690                 695                 700

Asn Thr Ala Gly Phe Ser Ser Ser Gln Ala Pro Asn Pro Val Asp Asp
705                 710                 715                 720

Glu Ser Trp Asp

<210> SEQ ID NO 5
<211> LENGTH: 372
<212> TYPE: PRT
<213> ORGANISM: Homo sapiens

<400> SEQUENCE: 5

Met Ser Lys Ser Glu Ser Pro Lys Glu Pro Glu Gln Leu Arg Lys Leu
1               5                   10                  15

Phe Ile Gly Gly Leu Ser Phe Glu Thr Thr Asp Glu Ser Leu Arg Ser
            20                  25                  30

```
His Phe Glu Gln Trp Gly Thr Leu Thr Asp Cys Val Val Met Arg Asp
        35                  40                  45

Pro Asn Thr Lys Arg Ser Arg Gly Phe Gly Phe Val Thr Tyr Ala Thr
    50                  55                  60

Val Glu Glu Val Asp Ala Ala Met Asn Ala Arg Pro His Lys Val Asp
65                  70                  75                  80

Gly Arg Val Val Glu Pro Lys Arg Ala Val Ser Arg Glu Asp Ser Gln
                85                  90                  95

Arg Pro Gly Ala His Leu Thr Val Lys Lys Ile Phe Val Gly Gly Ile
            100                 105                 110

Lys Glu Asp Thr Glu Glu His His Leu Arg Asp Tyr Phe Glu Gln Tyr
        115                 120                 125

Gly Lys Ile Glu Val Ile Glu Ile Met Thr Asp Arg Gly Ser Gly Lys
    130                 135                 140

Lys Arg Gly Phe Ala Phe Val Thr Phe Asp Asp His Asp Ser Val Asp
145                 150                 155                 160

Lys Ile Val Ile Gln Lys Tyr His Thr Val Asn Gly His Asn Cys Glu
                165                 170                 175

Val Arg Lys Ala Leu Ser Lys Gln Glu Met Ala Ser Ala Ser Ser Ser
            180                 185                 190

Gln Arg Gly Arg Ser Gly Ser Gly Asn Phe Gly Gly Arg Gly Gly
        195                 200                 205

Gly Phe Gly Gly Asn Asp Asn Phe Gly Arg Gly Gly Asn Phe Ser Gly
    210                 215                 220

Arg Gly Gly Phe Gly Gly Ser Arg Gly Gly Gly Gly Tyr Gly Gly Ser
225                 230                 235                 240

Gly Asp Gly Tyr Asn Gly Phe Gly Asn Asp Gly Gly Tyr Gly Gly Gly
                245                 250                 255

Gly Pro Gly Tyr Ser Gly Gly Ser Arg Gly Tyr Gly Ser Gly Gly Gln
            260                 265                 270

Gly Tyr Gly Asn Gln Gly Ser Gly Tyr Gly Gly Ser Gly Ser Tyr Asp
        275                 280                 285

Ser Tyr Asn Asn Gly Gly Gly Gly Phe Gly Gly Gly Ser Gly Ser
    290                 295                 300

Asn Phe Gly Gly Gly Gly Ser Tyr Asn Asp Phe Gly Asn Tyr Asn Asn
305                 310                 315                 320

Gln Ser Ser Asn Phe Gly Pro Met Lys Gly Gly Asn Phe Gly Gly Arg
                325                 330                 335

Ser Ser Gly Pro Tyr Gly Gly Gly Gly Gln Tyr Phe Ala Lys Pro Arg
            340                 345                 350

Asn Gln Gly Gly Tyr Gly Gly Ser Ser Ser Ser Ser Ser Tyr Gly Ser
        355                 360                 365

Gly Arg Arg Phe
    370
```

OPTOGENETIC TOOL FOR RAPID AND REVERSIBLE CLUSTERING OF PROTEINS

CROSS-REFERENCE TO RELATED APPLICATIONS

This application claims priority to U.S. Provisional Application Nos.: 62/347,677, filed Jun. 9, 2016; 62/362,889, filed Jul. 15, 2016; and 62/424,924, filed Nov. 21, 2016, which are herein incorporated by reference in their entirety.

STATEMENT REGARDING FEDERALLY SPONSORED RESEARCH OR DEVELOPMENT

This invention was made with government support under Grant No. DA040601 awarded by the National Institutes of Health. The government has certain rights in the invention.

REFERENCE TO SEQUENCE LISTING SUBMITTED ELECTRONICALLY

The Sequence Listing filed electronically herewith is also hereby incorporated by reference in its entirety (File Name: PRIN-50504-SL_ST25.txt; Date Created: Jul. 8, 2019; File Size: 14,931 bytes).

BACKGROUND OF THE INVENTION

Cellular function relies on coordinating the thousands of reactions that simultaneously take place within the cell. Cells accomplish this task in large part by spatio-temporally controlling these reactions using diverse intracellular organelles. In addition to classic membrane-bound organelles such as secretory vesicles, mitochondria and the endoplasmic reticulum, cells harbor a variety of membrane-less organelles. Most of these are abundant in both RNA and protein, and are referred to as ribonucleoprotein (RNP) bodies. Among dozens of examples include nuclear bodies such as nucleoli, Cajal bodies, and PML bodies, and cytoplasmic germ granules, stress granules and processing bodies ((Mao et al., 2011), (Anderson and Kedersha, 2009), (Buchan and Parker, 2009), (Handwerger and Gall, 2006)). By impacting a number of RNA processing reactions within cells, these structures appear to play a central role in controlling the overall flow of genetic information, and are also increasingly implicated as crucibles for protein aggregation pathologies ((Li et al., 2013), (Ramaswami et al., 2013)).

From a biophysical standpoint, these structures are remarkable in that they have no enclosing membrane and yet their overall size and shape may be stable over long periods (hours or longer), even while their constituent molecules exhibit dynamic exchange over timescales of tens of seconds (Phair and Misteli, 2000). Moreover, many of these structures have recently been shown to exhibit additional behaviors typical of condensed liquid phases. For example, P granules, nucleoli, and a number of other membrane-less bodies will fuse into a single larger sphere when brought into contact with one another ((Brangwynne et al., 2009), (Brangwynne et al., 2011), (Feric and Brangwynne, 2013)), in addition to wetting surfaces and dripping in response to shear stresses. These observations have led to the hypothesis that membrane-less organelles represent condensed liquid states of RNA and protein that assemble through intracellular phase separation, analogous to the phase transitions of purified proteins long observed in vitro by structural biologists ((Ishimoto and Tanaka, 1977), (Vekilov, 2010)). Consistent with this view, RNP bodies and other membrane-less organelles appear to form in a concentration-dependent manner, as expected for liquid-liquid phase separation ((Brangwynne et al., 2009), (Weber and Brangwynne, 2015), (Nott et al., 2015), (Wippich et al., 2013), (Molliex et al., 2015)). These studies suggest that cells can regulate membrane-less organelle formation by altering proximity to a phase boundary. Movement through such an intracellular phase diagram could be accomplished by tuning concentration or intermolecular affinity, using mechanisms such as posttranslational modification (PTM) and nucleocytoplasmic shuttling.

Recent work has begun to elucidate the molecular driving forces and biophysical nature of intracellular phases. Weak multivalent interactions between molecules containing tandem repeat protein domains appear to play a central role ((Li et al., 2012), (Banjade and Rosen, 2014)). A related driving force is the promiscuous interactions (e.g. electrostatic, dipole-dipole) between segments of conformationally heterogeneous proteins, known as intrinsically disordered protein or intrinsically disordered regions (IDP/IDR, which are typically, although not necessarily, also low complexity sequences, LCS). Hereinafter, the terms intrinsically disordered protein, intrinsically disordered region, and intrinsically disordered protein region are used interchangeably. RNA binding proteins often contain IDRs with the sequence composition biased toward amino acids including R, G, S, and Y, which comprise sequences that have been shown to be necessary and sufficient for driving condensation into liquid-like protein droplets ((Elbaum-Garfinkle et al., 2015), (Nott et al., 2015), (Lin et al., 2015)). The properties of such in vitro droplets have recently been found to be malleable and time-dependent ((Elbaum-Garfinkle et al., 2015), (Zhang et al., 2015), (Weber and Brangwynne, 2012), (Molliex et al., 2015), (Lin et al., 2015), (Xiang et al., 2015), (Patel et al., 2015)), underscoring the role of IDR/LCSs in both liquid-like physiological assemblies and pathological protein aggregates.

Despite these advances, almost all recent studies rely primarily on in vitro reconstitution, due to a lack of tools for probing protein phase behavior within the living cellular context. However, a growing suite of optogenetic tools have been developed to control protein interactions in living cells. The field has primarily focused on precise control over homo- or hetero-dimerization ((Toettcher et al., 2011), (Kennedy et al., 2010), (Levskaya et al., 2009)). But recent work suggests the potential of optogenetics for studying intracellular phases, demonstrating that light-induced protein clustering can be used to activate cell surface receptors (Bugaj et al., 2013), as well as to trap proteins into inactive complexes ((Lee et al., 2014), (Taslimi et al., 2014)).

To date, no platform has been provided which can be used to dynamically modulate intracellular protein interactions, enabling the spatiotemporal control of phase transitions within living cells. Such a platform would be highly desirable.

BRIEF SUMMARY OF THE INVENTION

The present invention is directed to protein constructs with the ability to induce and control reversible liquid-liquid phase separation, both globally and at specific subcellular locations. This system reveals that the location within the phase diagram can be used to dictate the material state of phase-separated IDR clusters, ranging from dynamic liquid droplets to arrested but reversible gels, which can over time mature into irreversible aggregates.

In the present invention, systems and methods are provided that utilize protein constructs with at least two regions fused to each other: (i) a light sensitive region containing a first segment (e.g., a protein sensitive to at least one wavelength of light) and (ii) a functional region containing a second segment (e.g., a low complexity sequence (LCS), an intrinsically disordered protein region (IDR), or one or more repeatable sequences).

Among the many different possibilities contemplated, a protein construct may also advantageously contain a desired protein to purify, or a fluorophore. In some embodiments, the second segment is an IDR, where the IDR is a portion of FUS, Ddx4, or hnRNPA1. In some embodiments, the protein sensitive to at least one wavelength of light used in the first segment contains a protein that is sensitive to visible light. In some embodiments, the protein sensitive to at least one wavelength of light used in the first segment is Cry2, Cry2olig, PhyB, PIF, light-oxygen-voltage sensing (LOV) domains, or Dronpa. It is contemplated that these protein constructs will be configured such that after being introduced into a living cell, typically through transfection with DNA encoding for the protein construct, which is then translated into the protein by the native cellular machinery, exposing the living cell with the protein construct to certain wavelengths of light will induce the protein constructs within the living cell to cluster. It is further contemplated that if these protein constructs contain cleavage tags, such as self-cleaving tags, Human Rhinovirus 3C Protease (3C/PreScission), Enterokinase (EKT), Factor Xa (FXa), Tobacco Etch Virus Protease (TEV), or Thrombin (Thr), then after a first induction, it may be advantageous to cleave and induce clustering again.

DETAILED DESCRIPTION OF THE INVENTION

Before the present invention is described in further detail, it is to be understood that the invention is not limited to the particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein.

It must be noted that as used herein and in the appended claims, the singular forms "a", "an", and "the" include plural referents unless the context clearly dictates otherwise.

Figure 1A:
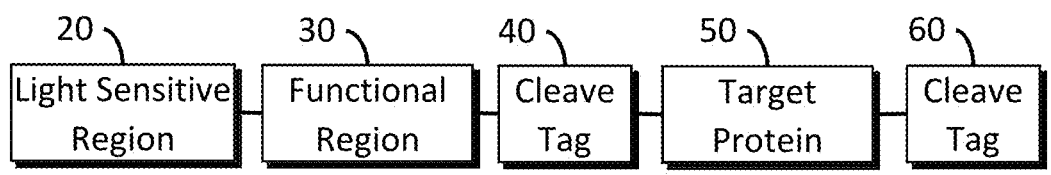
FIGS. 1A and 1B illustrate two embodiments of protein constructs.

FIG. 1A depicts a generalized embodiment of the present invention. A protein construct (10) will typically comprise a light sensitive region (20) and a functional region (30). The construct may also optionally comprise a first cleavage tag (40), a target protein (50), or a second cleavage tag (60). Typically, the second cleavage tag (60) will not be needed unless the construct is followed by another domain. The specific arrangement shown in FIG. 1A just serves as an example and other permutated arrangements can be employed.

The light sensitive region (20) typically includes a first segment comprising at least one protein sensitive to at least one wavelength of light. In preferred embodiments, this segment includes Cry2, Cry2olig, PhyB, PIF, light-oxygen-voltage sensing (LOV) domains, or Dronpa. In other embodiments, the segment includes a protein sensitive to a visible wavelength of light, typically including wavelengths from about 400 nm to about 800 nm.

The functional region (30), which is fused to the light sensitive region (20), may include a second segment, the second segment comprising one or more low complexity sequences, one or more intrinsically disordered protein regions (IDRs), one or more synthetic or natural nucleic acid binding domains, or at least one repeatable sequence, the repeatable sequence comprising a linker fused to at least one additional gene encoding at least one protein sensitive to at least one wavelength of light. In preferred embodiments, the protein construct comprises an IDR, where the IDR is a portion of a first protein selected from the group consisting of FUS (SEQ ID NO.: 3), Ddx4 (SEQ ID NO.: 4), and hnRNPA1 (SEQ ID NO.: 5). In some embodiments, the IDR comprises amino acids 1-214 of FUS, 1-236 of Ddx4, or 186-320 of hnRNPA1.

Figure 1B:
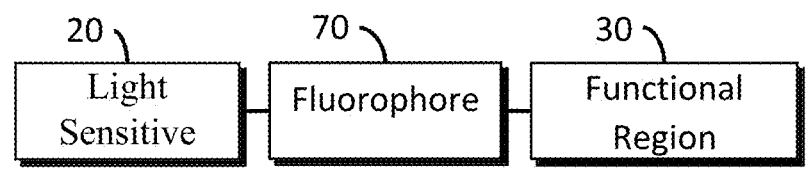

FIG. 1B shows an alternate arrangement of the protein construct, comprising an optional fluorophore (70). In FIG. 1B, the fluorophore (70) is fused between the light sensitive region (20) and the functional region (30), although other locations may be advantageous. In preferred embodiments, the fluorophore is mCherry, although the use of other fluorescent proteins is also envisioned, including but not limited to GFP variants.

An example of the protein construct was produced by fusing the "sticky" IDR from various proteins to the photolyase homology region (PHR) of Arabidopsis thaliana Cry2, a light-sensitive protein which is known to self-associate upon blue light exposure. This IDR-Cry2 fusion protein would recapitulate the modular domain architecture of many phase separating proteins, but confer tunable light-dependence to its multivalent interactions.

The approach of replacing the multi-valent interaction domains of FUS and other IDR-containing RNA binding domains with a light-activatable Cry2(WT) motif is inspired by native mechanisms utilized by cells to control intracellular phase transitions. Phase separation in cells appears to be regulated in two distinct but complementary ways: 1) changing the concentration of protein constructs, for example by protein translation, altered degradation, or nucleocytoplasmic shuttling, and 2) changing their intermolecular interaction strengths, for example through PTMs, particularly phosphorylation which deposits a negative charge on S, T, or Y residues, which are commonly found in IDRs driving phase separation. Indeed, FUS is found in stress granules, one type of membrane-less body whose assembly depends on PTMs and protein concentration, and which has been suggested to assemble by regulated intracellular phase separation.

DNA fragments encoding IDRs of human FUS (residues 1-214) and human hnRNPA1 (residues 186-320) were amplified by PCR using FUS cDNA (GeneCopoeia, GC-F0952) and pET9d-hnRNP-A1 (Addgene plasmid #23026), respectively. A gene for the IDR of human dx4 (residues 1-236) was synthesized (Integrated DNA Technologies). Sequences for mCherry and Cry2olig (Addgene plasmid #60032) were cloned into the pHR lentiviral backbone to generate the pHR-mCh-Cry2olig plasmid. A site-directed mutagenesis was then performed to produce the Cry2WT version. For IDR-fusion Cry2 plasmids, DNA fragments encoding the IDRs were inserted into the linearized pHR-mCh-Cry2WT (or Cry2olig) backbone using In-Fusion Cloning Kit (Clontech). The resulting constructs were fully sequenced to confirm the absence of unwanted substitutions.

These constructs were introduced into living cells. mCherry-labeled Cry2 PHR (hereafter: Cry2WT) was first expressed in NIH 3T3 cells along with a few other variants. NIH 3T3 cells were cultured in 10% FBS (Atlanta Biological) in DMEM (Gibco) supplemented with penicillin, streptomycin and GlutaMAX (Gibco) at 37° C. with 5% $CO_2$ in a humidified incubator. To produce stable cell lines expressing cry2 fusion constructs, lentiviral constructs were transfected with FuGENE (Promega), following the manufacturer's recommended protocol, into 293T cells that had been plated in the 6-well dishes 1 day prior to the transfection. Viral supernatants were collected 2 d after transfection and passed through a 0.45-μm filter to remove cell debris. NIH 3T3 cells plated at ~70% confluency in the 6-well dishes were infected by adding 0.4-1 ml of filtered viral supernatant directly to the cell medium. Viral medium was replaced with normal growth medium 24 h after infection.

The cells were then induced to cluster with blue light. Consistent with previous reports, Cry2WT alone showed little clustering upon blue light activation. Strikingly, fusing the N-terminal IDR of FUS ($FUS_N$) to Cry2WT (hereafter optoFUS) leads to rapid blue-light dependent cluster assembly in most cells. Similar results were seen upon fusing the C-terminal IDR of the ALS-related RNA binding protein hnNRNPA1 (optoHNRNPA1), or the N-terminal IDR of Ddx4 (optoDDX4), both of which have been reported to drive liquid-liquid phase separation.

Figure 2A:
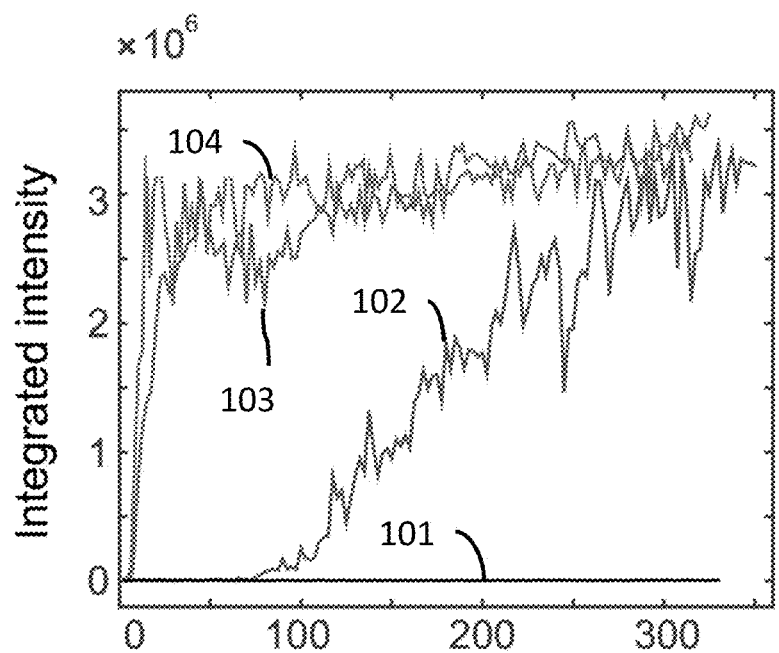
FIG. 2A is a graph of assembly rates for various protein constructs, including constructs without a light-sensitive region (101), Cry2olig-only constructs (102), optoFUS constructs (103), and Cry2olig-FUS$_N$ constructs (104).
Figure 2B:
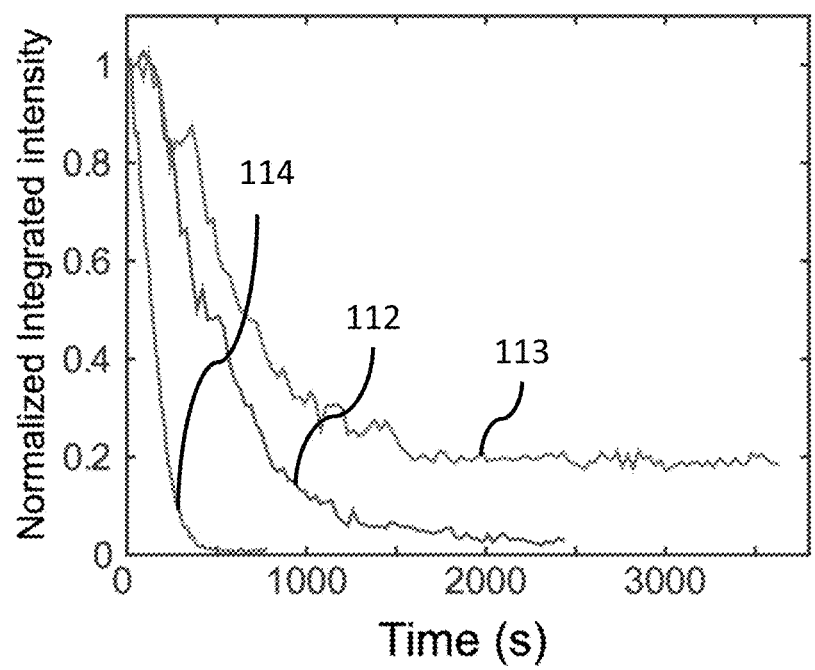
FIG. 2B is a graph of disassembly rates for various protein constructs, including Cry2olig-only constructs (112), Cry2olig-FUS$_N$ constructs (113), and optoFUS constructs (114).

As shown in FIG. 2A, the optoFUS construct (103) exhibits ~9-fold faster assembly of clusters than Cry2olig constructs (102), under similar expression level and activation conditions. Referring to FIG. 2B, it is also noted that the optoFUS constructs (114) disassemble ~3-fold faster than Cry2olig constructs (112). Interestingly, the assembly of Cry2olig clusters is also dramatically enhanced when it is fused to $FUS_N$ (FIG. 2A, element 104). However, the disassembly of these $FUS_N$-Cry2olig clusters (113) is now much slower than for Cry2olig alone (112). Moreover, these clusters (113) do not completely dissolve, even after >1 hour without light activation.

Liquid droplets tend to adopt round shapes due to surface tension. Consistent with this feature of liquids, optoFUS clusters have round morphologies. A second feature common to liquid phase droplets is that the protein constructs within undergo dynamic exchange with the surrounding solution. Fluorescence recovery after photobleaching (FRAP) experiments, involving bleaching the mCherry signal, shows a nearly complete recovery of the fluorescence signal, with a recovery time scale of 140±10 s. Finally, in non-biological systems, small phase separated droplets can dissolve at the expense of larger droplets, an effect known as Ostwald ripening. Ostwald ripening is frequently observed in the optoFUS clusters, particularly within those that assemble within the cell nucleus. Together, these data strongly suggest that optoFUS clusters formed upon blue light exposure are liquid phase droplets.

These liquid-like behaviors suggest that optodroplet assembly may represent light-inducible liquid-liquid phase separation within the cell. A light-induced increase in Cry2 self-association affinity could represent a controllable change to the effective valency of the constructs. In the presence of light, each FUS-Cry2 fusion protein can associate with other monomers through Cry2-Cry2 or FUS-FUS interactions, whereas only FUS-FUS interactions would be possible in the dark. In this physical picture, the light-increased avidity would result in the crossing of a phase boundary and consequent initiation of liquid-liquid phase separation.

The concentration of light-activated optoFUS can be changed using at least two independent methods: 1) by changing the total concentration of optoFUS protein constructs molecules within the cell, and 2) by changing blue light intensity. If the assembly mechanism is liquid-liquid phase separation, then droplet formation should depend on both optoFUS concentration and light activation level. Consistent with this, droplet formation shows a strong dependence on blue light activation intensity. For an activation protocol which begins at a very weak power, initially no cells exhibit droplets, even after continuous weak blue light activation for 16 min. However, when the blue light power was tripled, those cells which express high levels of the optoFUS construct now assemble droplets. Distinct and spatially separated droplets slowly nucleate and then grow in size; qualitatively, this behavior is very similar to the well-known nucleation and growth regime observed in shallow-quench phase transitions—i.e., in systems which are only moderately supersaturated.

The dependence of droplet assembly kinetics on the total concentration of optoFUS was also tested. Blue light power was fixed and assembly was examined in cells with different expression levels; intracellular optoFUS concentrations ranging from about 0.2 to about 13 µM were used, comparable to the estimated intracellular concentration of endogenous FUS: ~1-10 µM. Consistent with the results obtained for varying blue-light activation, the lowest expressing cells do not form droplets at all. Interestingly, for cells that do form droplets, the higher the expression level, the faster the assembly kinetics. Thus, both the total optoFUS concentration and blue light intensity collectively affect light-induced droplet formation.

Finally, it was determined if the opposing effects from these two parameters can compensate each other to give rise to similar assembly dynamics. Indeed, higher expressing cells exposed to weaker blue light show similar clustering kinetics as lower expressing cells exposed to stronger light. Taken together, these data suggest that the concentration of light activated optoFUS can be used for controlling droplet formation.

A simple kinetic framework for measuring the concentration of activated protein constructs, and its relationship to the onset of droplet condensation, was developed to quantitatively test whether this system reflects light-controllable phase separation. We assume that the inactivated state undergoes a first-order reaction to the activated state, with a reaction rate proportional to light intensity, according to $k_1=k_{act}*[blue]$, where $k_{act}$ is an activation rate constant and [blue] is the intensity of activating blue light. The activated protein constructs can also convert back to the inactivated state, at a rate given by $k_2$. In this model, blue light exposure increases the concentration of activated, self-associating protein constructs, which drives global phase separation upon exceeding the saturation concentration, i.e., when $C_{act}>C_{sat}$.

Figure 3A:
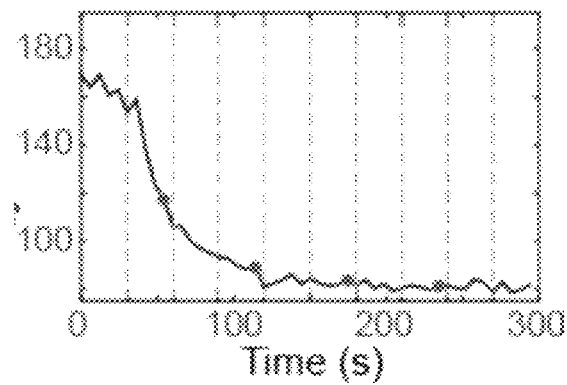
FIGS. 3A and 3B are graphs of the temporal evolution of background concentrations outside clusters, $C_{bg}$, for certain cells, where the activation interval is T=30 s (FIG. 3A) or T=180 s (FIG. 3B). Dots denote time points when cell images were taken and dashed lines represent time points for blue light activation.
Figure 3B:
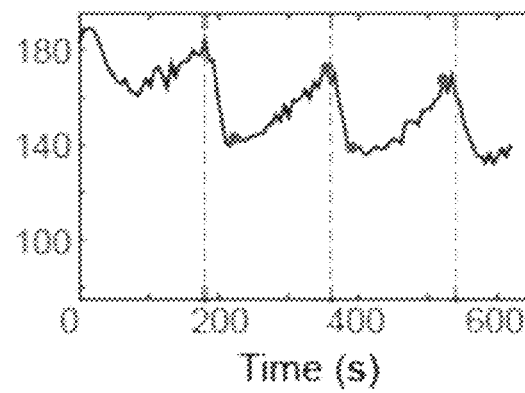

A series of activation protocols were employed with different activation intervals and blue light power. Cycles of light followed by dark were utilized, since this provides the ability to probe both the activation rate constant, $k_{act}$, and the inactivation rate constant, $k_2$. When optoFUS cells are exposed to a pulse train of activating light stimuli with high enough intensity, cells form droplets typically after a short lag phase. As protein constructs are recruited into droplets, the background concentration (fluorescence intensity) outside of droplets decreases. As shown in FIGS. 3A and 3B, when the interval between consecutive pulses is relatively long (e.g., T=180 s, shown in FIG. 3B) cycles of partial assembly and disassembly are observed, but for intervals shorter than 1 min (e.g., T=30 s, shown in FIG. 3A) the background intensity exhibits a monotonic decay to a steady state, Cbg,st.

Figure 3C:
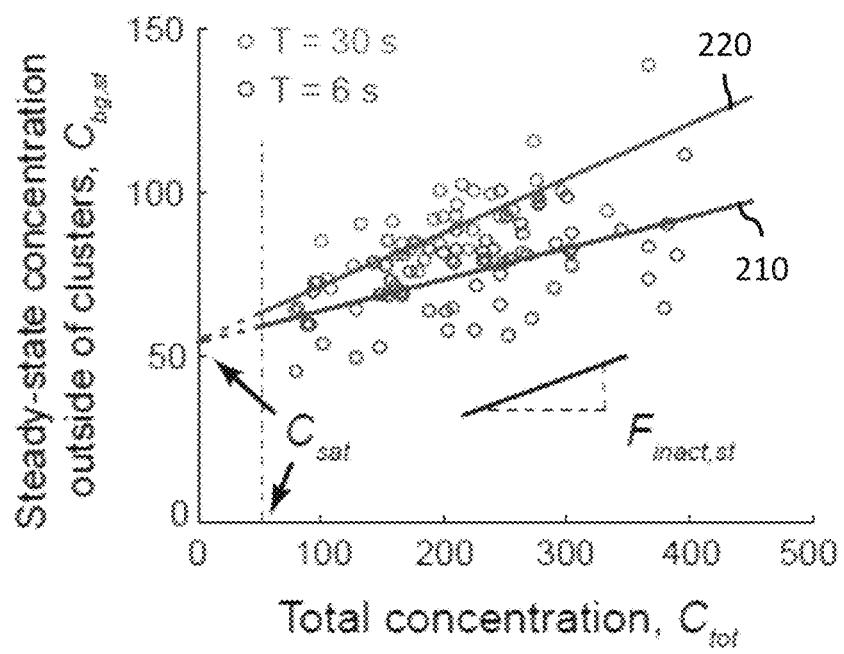
FIG. 3C is a graph indicating the steady-state background fluorescence intensities of individual cells (open circles) under the given activation interval increase linearly (solid lines) with total concentration of protein constructs, as well as best fit lines for interval times of T=6 s (210) and T=30 s (220).
Figure 3D:
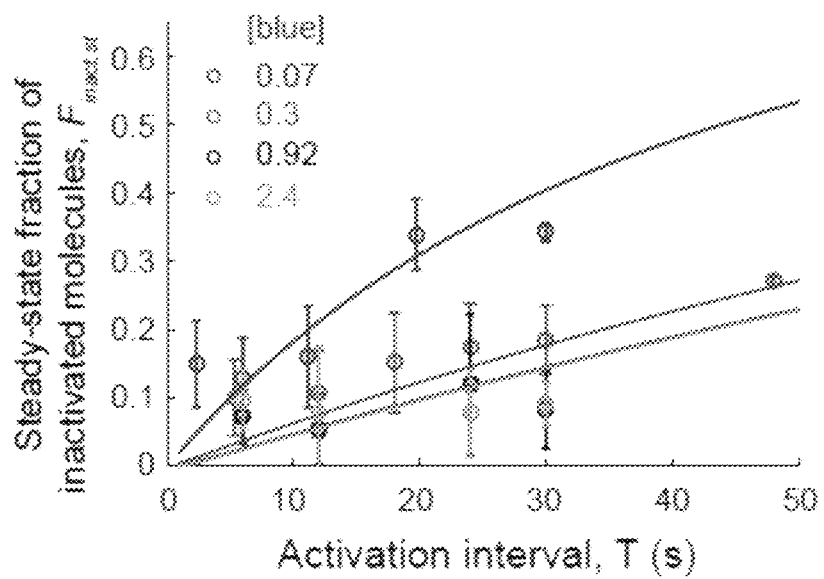
FIG. 3D is a graph indicating the impact of activation interval on the steady-state fractions of inactivated protein constructs for 4 different amounts of 488 nm blue light (0.07 µW, 0.3 µW, 0.92 µW, and 2.4 µW); solid lines denote a global fit to data using the kinetic model.

In the simplest phase transition model, the steady-state background concentration is equal to a sum of the concentration of inactivated protein constructs, $C_{inact,st}$, and the activated protein constructs outside clusters, $C_{sat}$. Expressing $C_{inact,st}$ as a fraction $F_{inact,st}$ of the total concentration: $C_{inact,st}=F_{inact,st}C_{tot}$, the steady-state background concentration is thus $C_{bg,st}=F_{inact,st}C_{tot}+C_{sat}$. Consistent with this model prediction, the steady-state background concentration of activated optoFUS cells increases linearly with total concentration. Moreover, as shown in FIG. 3D, varying activation intervals yield different slopes ($F_{inact,st}$), but converge to a similar y-intercept ($C_{sat}$, corresponding to ~1.4 µM), consistent with the saturation concentration representing an intrinsic property of the optoFUS construct. Indeed, the identical activation protocol, when applied to optoDDX4 cells, yields 2-fold lower $C_{sat}$, implying stronger intermolecular interaction between Ddx4 IDRs.

Figure 3E:
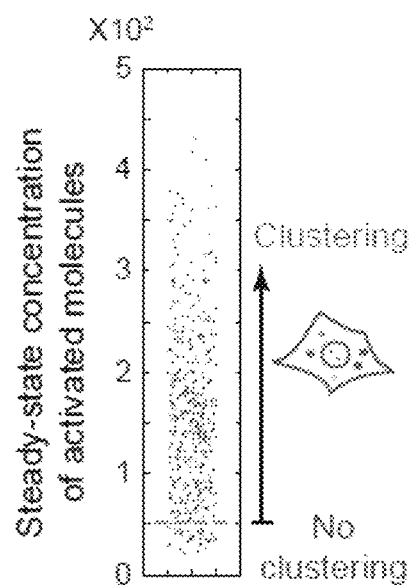
FIG. 3E is a depiction of the calculated steady-state concentrations of activated protein constructs, showing a clear concentration threshold for light-mediated clustering, and a dotted horizontal line indicating the saturation concentration.

This kinetic framework can be utilized to quantify the rate constants for activation. We first computed the steady-state fraction of inactivated protein constructs for each cell using the relationship, $F_{inact,st}=(C_{bg,st}-C_{sat})/C_{tot}$, and the measured saturation concentration. FIG. 3C shows the fraction of inactivated protein constructs for intervals of T=6 s and T=30 s, as well as best fit lines for T=6 s (210) and T=30 s (220). In agreement with the model predictions, this illustrates that the fraction of inactivated protein constructs increases with either longer activation intervals or weaker blue light intensity. This can be well-fit to the functional dependence predicted by the model, yielding values for the rate constants, $k_{act}$=7.4±4.7 µW$^{-1}$ s$^{-1}$ and $k_2$=0.011±0.005 s$^{-1}$. Moreover, this also agree with the model prediction that at high enough power, the inactivated fraction becomes independent of blue light intensity, since all protein constructs already populate the activated state. Finally, phase separation should only occur if the total concentration of activated protein constructs exceeds the saturation concentration, Csat. This prediction is in good agreement with data for this embodiment, which show a sharp concentration threshold for the activated protein constructs, below which no cytoplasmic clusters were observed (See FIG. 3E).

The preceding experiments and theoretical analysis show that fusing, for example, self-associating IDRs to the light activation domain of Cry2WT enables light-activated phase separation. However, it is also possible to modulate the assembly dynamics by changing the light activation domain. Previously, a point mutant version of Cry2 (E490G), known as Cry2olig, was shown to exhibit significant clustering The assembly of Cry2olig is also dramatically enhanced when it is fused to FUSN, exhibiting ~9-fold faster assembly under similar expression level and activation conditions, comparable to the rapid assembly of the optoFUS construct (i.e. FUSN-Cry2WT).

Applying the same method of cycled light activation described above, it was found that there is also a saturation concentration of FUSN-Cry2olig. However, the saturation concentration of FUSN-Cry2olig is 5-fold lower than optoFUS, consistent with the point mutation (E490G) in Cry2olig increasing homo-interaction strength. Moreover, the inactivation rate of FUSN-Cry2olig is 5-fold slower than optoFUS, consistent with the previous findings. Thus, utilizing IDR fusions with various other self-associating optogenetic proteins can be used to tune the dynamics of light-induced intracellular phase separation.

While the above example utilizes IDRs, the functional region may also utilize other proteins, such as synthetic or natural nucleic acid binding domains. Many RNA binding proteins contain self-associating IDRs or LCSs that can drive phase separation. However, additional RNA binding domains can enhance phase separation via multivalent interactions with RNA. For example, FUS is an ALS-related RNA binding protein involved in diverse nucleic acid processing including DNA repair, transcription and pre-mRNA splicing. While the self-associating N-terminal IDR of FUS has been shown to be necessary and sufficient for liquid-liquid phase separation, C-terminal RNA binding domains appear to further promote phase separation. In preferred embodiments, the synthetic or natural nucleic acid binding domains utilizes RNA recognition motifs (RRM), double-stranded RNA binding domains (dsRBD), S1, zinc finger binding domains, YT521-B homologies (YTH), DNA and RNA helicase domains, Pumilio, or S-adenosylmethionine (SAM) structures.

Rapid growth and fast inactivation lead to localized phase separation. Local changes in molecular interaction strength can induce intracellular phase separation at specific subcellular locations, as in the case of P granule condensation during *C. elegans* embryo development. By controlling the spatial distribution of blue light, analogous local phase separation is achievable. When the corners of individual optoFUS cells were locally illuminated, droplets rapidly assembled near the activation zone, with a wave of droplet assembly propagating outward, but only over a short range near the activation zone. This was verified with single line activation, localized in time and space. When a line pulse was applied to optoFUS cells, droplets immediately form along the activation line. The width of cluster distribution was maintained over a narrow band, before all droplets began disassembling within a few minutes.

To quantitatively elucidate the dynamics of phase separation upon localized activation, a simplified coarse-grained model was developed that is consistent with a mesoscale model. This model describes the concentration of activated protein constructs, c(x), as well as the droplets they nucleate, which are characterized by the single field variable $\theta_d(x,t)$ that represents the volume fraction of droplets within a given spatial volume. The model predicts that the steady-state droplet profile width for continuous localized activation is given by: $x_0^{SS} \sim \sqrt{D/k_2} \ln [k_1 E/(c_{sat}\sqrt{D(k_1+k_2)})]$, indicating that the primary factor is the reaction-diffusion length scale, $\sqrt{D/k_2}$, where D is the molecular diffusion coefficient in cytoplasm. Thus, diffusion of activated monomers will tend to oppose localized droplet formation, while rapid reversion to the dark state would sharpen droplet localization patterns. Numerical simulations of the model support this physical picture by reproducing the evolution time and extent of experimentally-observed droplet profiles, provided heterogeneous (seeded) nucleation kinetics are employed; interestingly, the observed behaviors are not consistent with homogeneous nucleation.

Figure 4:
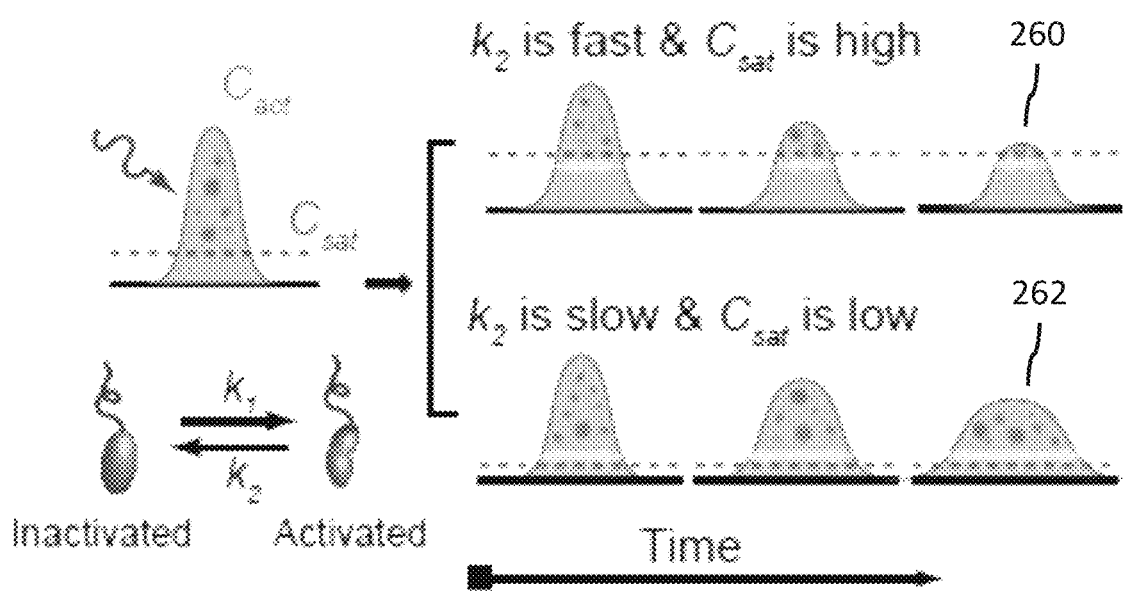
FIG. 4 is a schematic diagram illustrating the broadening effects of slower inactivation kinetics and lower $C_{sat}$ on the localized phase transition, and specifically the localized phase transitions given fast inactivation kinetics and high $C_{sat}$ (260) and the localized phase transition given slow inactivation kinetics and low $C_{sat}$ (262).

This coarse-grained model predicts that the 5-fold slower inactivation rate ($k_2$) and 5-fold lower $c_{sat}$ exhibited by FUSN-Cry2olig relative to optoFUS would limit the ability to localize droplet assembly (See FIG. 4, compare diameter of localized phase transition 260 vs localized phase transition 262). Consistent with the model prediction, in FUSN-Cry2olig cells, clusters first rapidly appeared at the localized activation zone, but a wave of cluster formation then propagated slowly across the entire cell; a single line pulse activation also displayed a broader cluster distribution than for optoFUS. Moreover, cells expressing Cry2olig alone exhibited a long lag time, followed by the concomitant appearance of clusters even far away from the activation zone. These data demonstrate that localized phase separation seen in optoFUS depends on the rapid growth conferred by the IDR, combined with the relatively fast inactivation kinetics of Cry2WT.

Figure 5A:
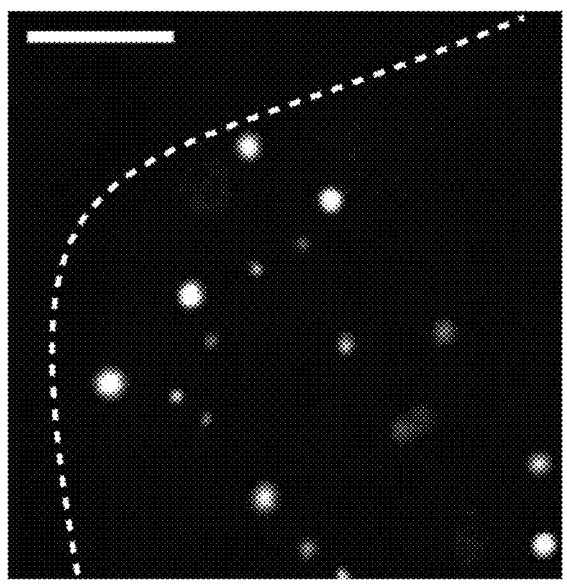
FIGS. 5A and 5B are images of the distinct morphology of phase separated optoFUS clusters for shallow (5A) and deep (5B) supersaturation.
Figure 5B:
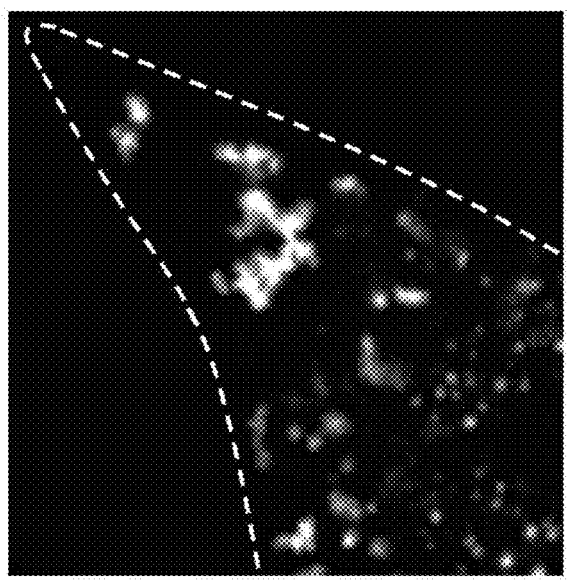
Figure 6:
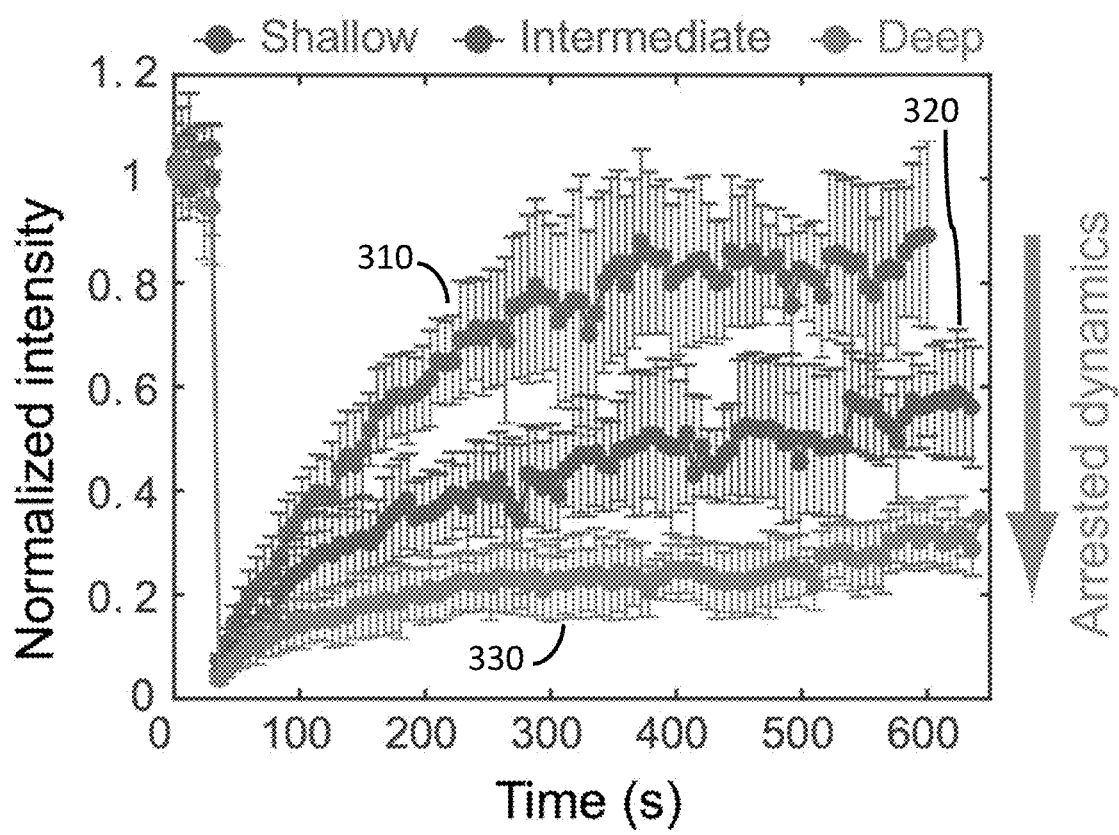
FIG. 6 is a graph of FRAP recovery curves of optoFUS clusters formed with varying supersaturation depths, including shallow quenching depths (310), intermediate quenching depths (320), and deep quenching depths (330).

The location within the phase diagram provides a degree of control over material properties and aging potential of clusters that are induced. In simple non-biological systems, quenching deep into the two phase region, corresponding to a high degree of supersaturation, can lead to condensation of assemblies with arrested dynamics, typically referred to as gels or glasses. Similar arrested dynamics can be observed in living cells, by exposing cells with similar expression levels to varying blue light intensity, thus moving into different depths beyond the phase boundary. For shallow quenching, cells typically showed no clustering during a long lag period of ~100 seconds, followed by slow phase separation. As the quenching depth increases, the lag period shortens; for sufficiently high blue light activation, phase separation is initiated immediately after activation. Notably, as shown in FIGS. 5A and 5B, while shallow quenching (FIG. 5A) tends to give rise to the relatively round droplet-like assemblies such as those described above, deep quenching (FIG. 5B) leads to the formation of structures with highly irregular shapes. Small diffraction-limited puncta that appeared immediately upon blue light exposure grew in size over time, in large part due to sticking to one another, forming highly branched elongated structures. Consistent with the apparent gel-like nature of these assemblies, FRAP measurements reveal that the major fraction of protein constructs within these clusters do not exchange with the surrounding cytoplasm. Indeed, as shown in FIG. 6, as the quenching depth increases from shallow (310) to intermediate (320) to deep (330), the fraction of recovery decreases, implying an increase in the solid fraction. Thus, the material state of light-activated assemblies can be tuned by controlling the cytoplasmic location within the phase diagram.

The assembly of structures such as P granules, Ddx4 puncta, and nucleoli also appear to be controlled through a combination of PTMs and protein concentration levels, which would similarly allow cells to move their cytoplasm into different regions of a high-dimensional phase diagram.

Referring again to FIG. 1, when cleavage tags are utilized, at least one cleavage tag (40) is typically inserted between the functional region and a protein that has been targeted for, e.g., purification. A wide variety of cleavage tags are envisioned, including but not limited to: self-cleaving tags, Human Rhinovirus 3C Protease (3C/PreScission), Enterokinase (EKT), Factor Xa (FXa), Tobacco Etch Virus Protease (TEV), and Thrombin (Thr).

Figure 7:
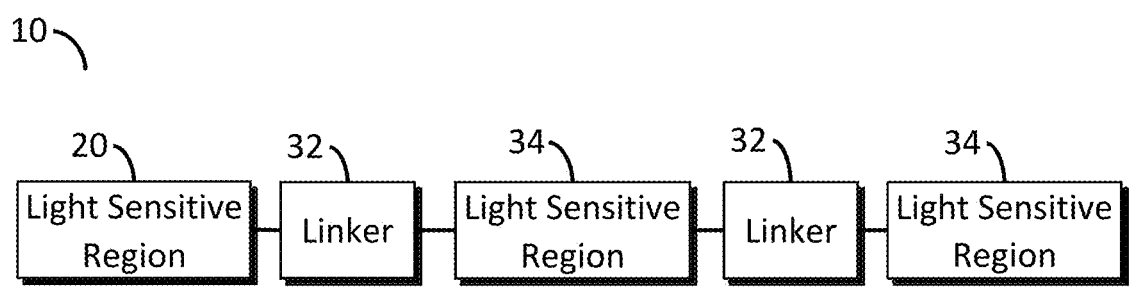
FIG. 7 illustrates an embodiment of protein construct using repeatable units.

The functional region may also utilize a repeatable element. As shown in FIG. 7, the functional region can comprise repeatable units of a linker fused to a gene encoding a protein sensitive to light, where the number of repeats is typically, although not limited to, 1 to 20. Preferably the number of repeats is from 2 to 9, and more preferably the number of repeats is about 4.

Figure 8A:
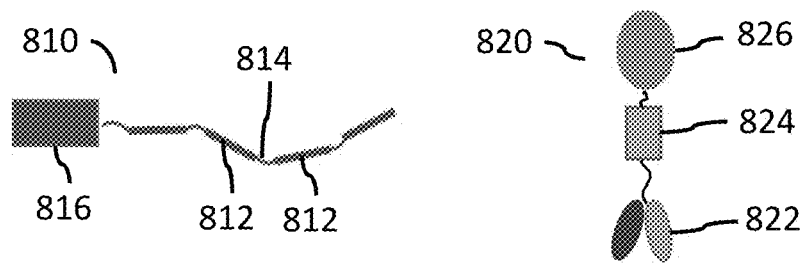
FIG. 8A is an illustration of a two-component system leading to light-activatable repeats, where a first component (810) includes four tandem copies of a GCN4 peptide (812) separated by linkers (814), which are fused to a fluorophore (816), and a second component (820) with functional region (822) that includes scFV-GNC4, a fluorophore (824) and a light sensitive region (826) that includes Cry2.
Figure 8B:
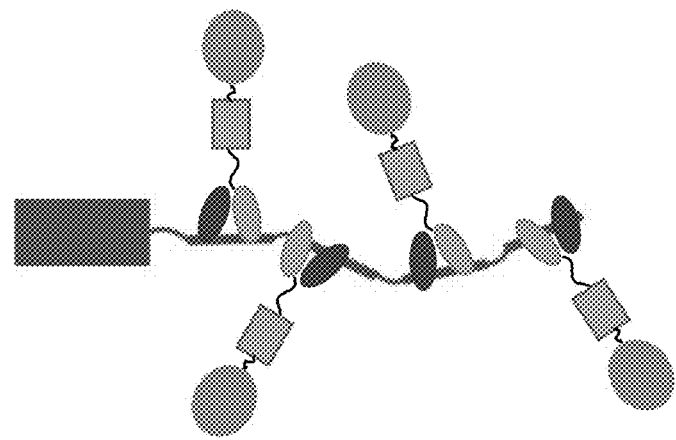
FIG. 8B illustrates the self-assembled construct shown in FIG. 8A in the absence of activating light.
Figure 8C:
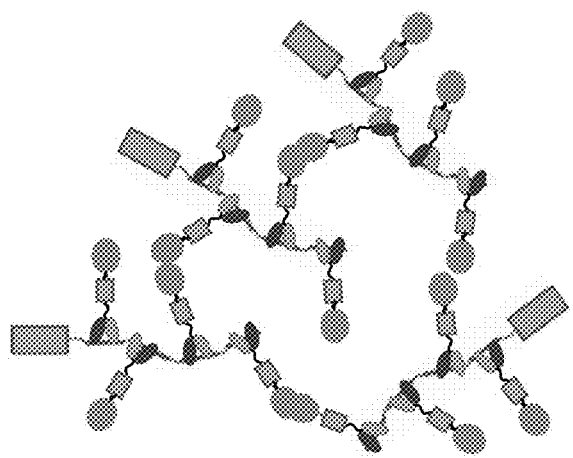
FIG. 8C is an illustration showing the resulting clusters of protein constructs upon light activation.

Although many variants are envisioned, FIGS. 8A-C depict one example involving a first protein (810) construct which may have, for example, 4 tandem copies (812) of the GCN4 peptide (SEQ ID NO.: 1: EELLSKNYHLENE-VARLKK), each separated by linkers (814), which is then fused to a fluorophore (816). A second protein construct (820) may comprise scFV-GNC4-sfGFP-Cry2, where the functional region comprises scFV-GNC4 (822), sfGFP (824) acts as a fluorophore, and the light sensitive region comprises Cry2 (826). As depicted in FIG. 8B, without light, the second protein construct binds to the peptide binding sites on the first protein construct. Upon exposure to light, Cry2-Cry2 binding occurs, creating large clusters of the first and second protein constructs, shown in FIG. 8C.

Figure 8D:
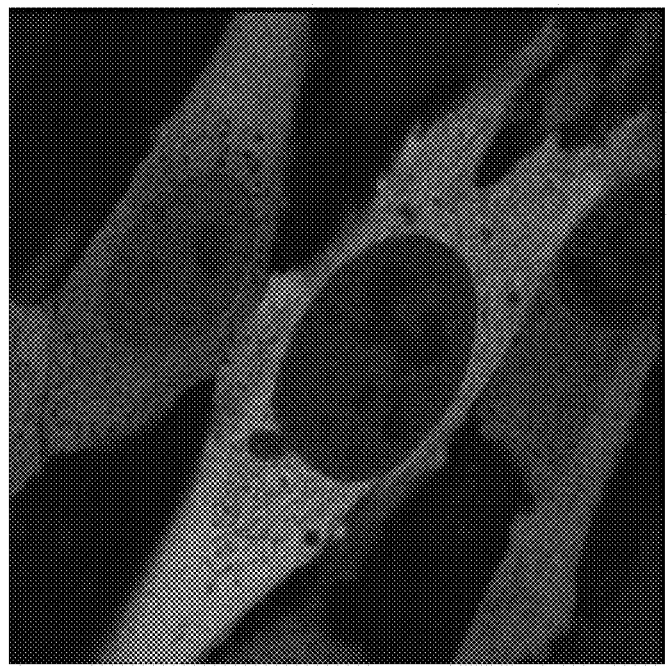
FIG. 8D illustrates several NIH3T3 cells, some of which only express mCh-10XGCN4 but not scFV-GNC4-sfGFP-Cry2 (red cells), while others express both constructs (yellow cells).
Figure 8E:
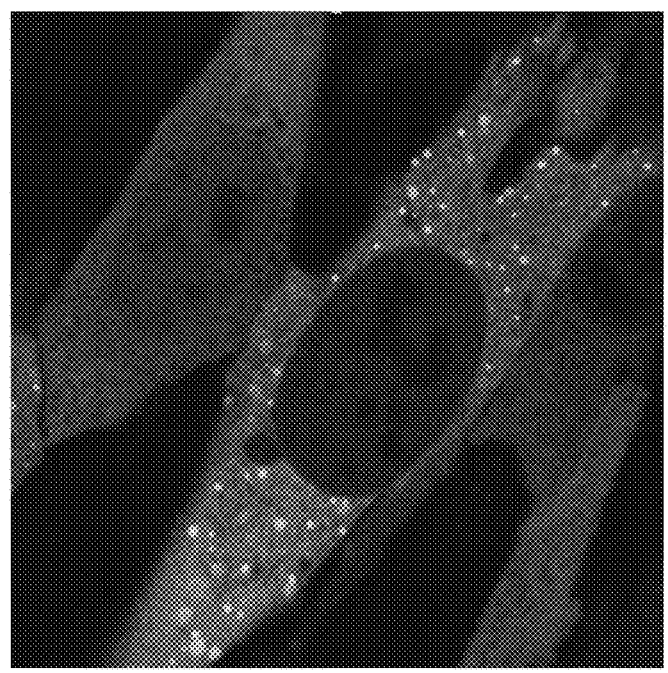
FIG. 8E illustrates that upon light activation, yellow cells expressing both constructs exhibit light-activated clustering, while red cells expressing only mCh-10XGCN4 do not show any clustering.

FIG. 8D illustrates several NIH3T3 cells, some of which only express mCh-10XGCN4 but not scFV-GNC4-sfGFP-Cry2 (red cells), while others express both constructs (yellow cells). FIG. 8E illustrates that upon light activation, yellow cells expressing both constructs exhibit light-activated clustering, while red cells expressing only mCh-10XGCN4 do not show any clustering, consistent with the fact that clustering for the system in the example above would require Cry2 multimerization.

At least three protein construct system configurations are also envisioned that utilize multiple, different protein constructs comprising repeatable units. In the first configuration, a system is envisioned wherein the light sensitive regions are identical, but the number of repeating units is different. An example of this is a Cry2(-linker-Cry2)$_n$ arrangement, where the system contains three types of constructs, where n=2, 5, and 12. Although preferred embodiments utilize between about 2 and about 12 repeatable units, it is envisioned that a protein construct can utilize any number of repeatable units.

In the second configuration, at least two types of constructs are used, each having the same number of repeating units, but having different light sensitive regions. In a preferred embodiment, the system uses two types of constructs, each comprising at least a portion of one of a pair of proteins, such as Cry2-CIB, PhyB-PIF, or iLID-SspB.

This second configuration is based on the recognition that by changing the affinity and valency of protein-protein interactions we can control both the phase behavior and properties of the resulting droplets. The PhyB/PIF optogenetic system is able to change interaction affinities by varying the ratio of 650 nm and 750 nm light applied to the PhyB protein. The range of achievable interaction affinities is broadly tunable—individual PhyB-PIF interactions are very weak under pure 750 nm light (>100 µM), but very strong under pure 650 nm light (<100 nM). By changing the 650/750 nm ratio, any intermediate affinity can be attained. By using PhyB and PIF constructs with different number of repeats, the multivalency can be further tuned to induce phase separation under even modest concentrations (<1 µM). Other light-activatable proteins may also be used, such as the PHR domain of the protein Cry2. When activated with blue light (488 nm), these multimerized Cry2 constructs will phase separate into droplets or gel-like structures. This enables building light induced clusters, either within living cells or in vitro, with potential applications from perturbing intracellular organization, to purifying proteins through fusion with affinity purification tags and centrifuging the phase separated droplets.

In the case where the light activatable domains are PhyB/PIF pairs, one can express and purify in *E. coli* (BL21) polymers (e.g., 5-mers) of poly PhyB (PhyB$_5$), and 5-mers of poly PIF (PIF$_5$). It is also advantageous to include, for example, a TEV-cleavable His-tag, although other known methods for cleaving are envisioned.

Figure 9A:
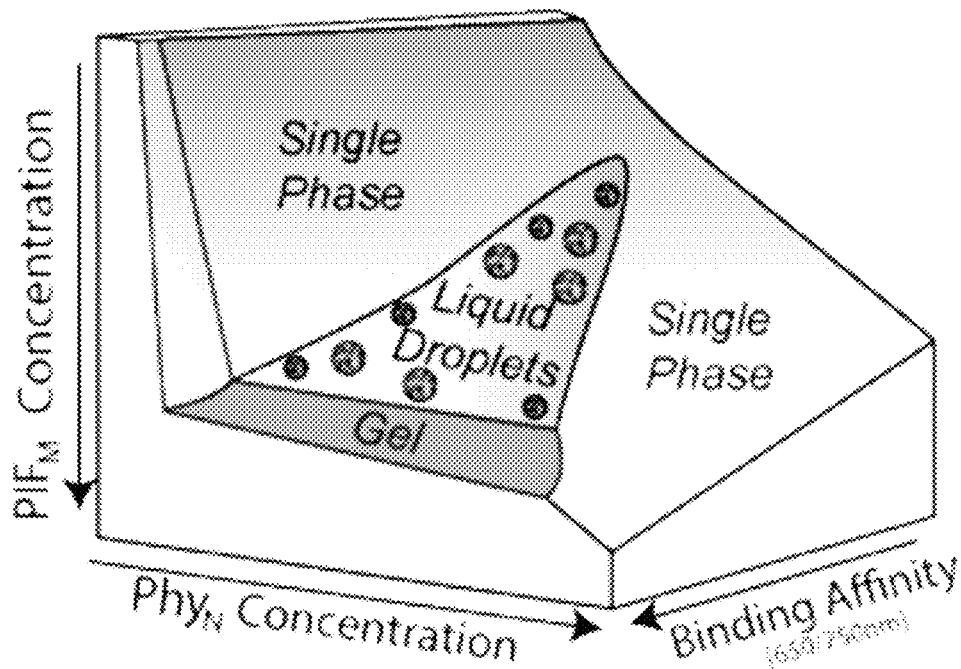
FIG. 9A is an illustration of an example 3D phase diagram as a function of the concentration of a particular repeat number for illustration purposes showing PhyB$_N$+PIF$_M$, and apparent binding affinity, controlled by the 650/750 nm light ratio.

These constructs can then be mixed, and illuminated with defined ratios of 650/750 nm light from computer-controlled LED sources. Lower repeat numbers, e.g. PhyB$_3$ and PIF$_3$, as well as higher repeat numbers, e.g. PhyB$_{10}$ and PIF$_{10}$ may also be used. Moreover, it is possible to use mixed repeat number solutions, i.e., PhyB$_M$+PIF$_N$, where M≠N under different light activation settings (650/750 nm), to optimize for maximum optical control of assembly under different physiological protein concentrations ([PhyB$_M$], [PIF$_N$] ≤µM); using where M≠N allows for selective sequestration. The precise concentrations and repeat number of the various constructs, together with the degree of light activation, allows for control over the phase behavior and properties of the resulting assembles, which may be liquid like or more solid like, as shown in the example schematic in FIG. 9A.

Figure 9B:
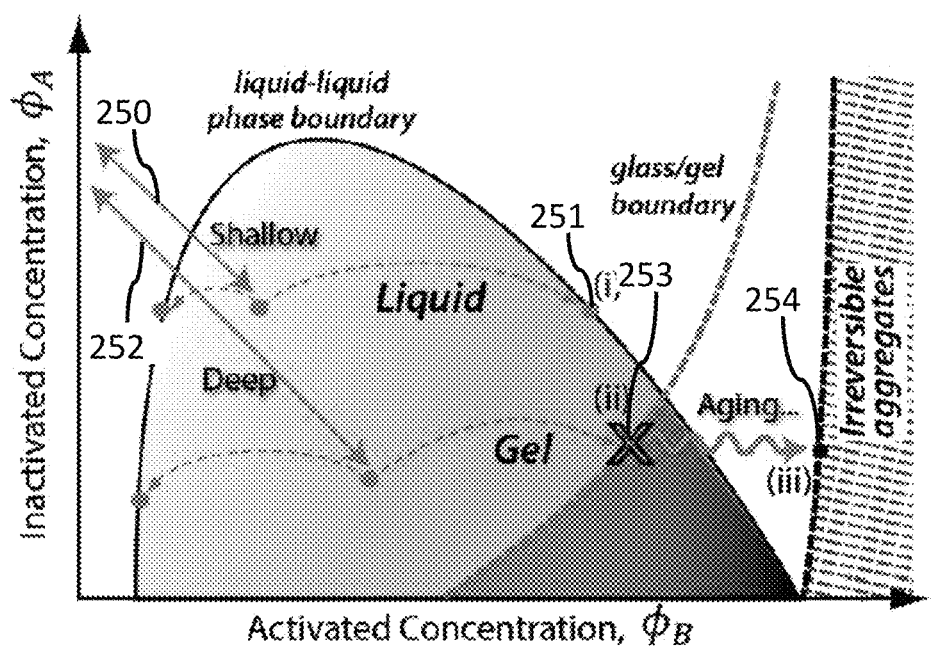
FIG. 9B is another illustration of a phase diagram, showing the process that (i) occurs with a shallow quenching depth (250), resulting in the formation of a liquid droplet (251); and (ii) occurs with a deep quenching depth (252), resulting in the formation of solid-like gels (253) which can lead to the formation of irreversible aggregates (254).

Conversion of molecular species from weak self-association state to high self-association one, for example through post-translational modification or exposure of RNA in RNP complexes, leads to liquid-liquid phase separation. As shown in FIG. 9B, when the depth is shallow, this process follows the green path (250) to produce liquid droplets (251). Deep supersaturation along the red path (252) results in the formation of solid-like gels (253), with arrested molecular dynamics. Gels are initially reversible, but slow dynamics within promote the formation of irreversible aggregates over time (254).

Figure 10:
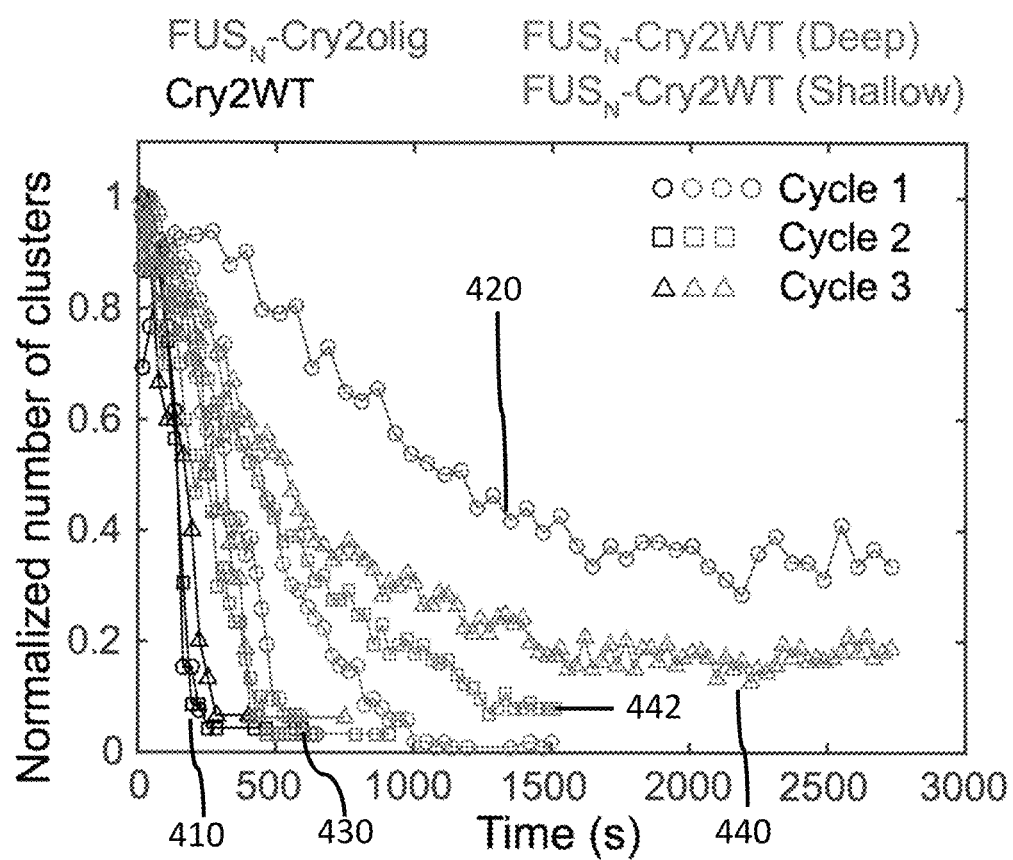
FIG. 10 is a graph of a normalized number of clusters for four different constructs during the first, second, or third cycle of quenching, including (i) constructs with Crt2WT but without FUS$_N$ (410) during first cycle; (ii) FUS$_N$-Cry2olig constructs (420) during first cycle; (iii) OptoFUS constructs with shallow quench depths (430) during first cycle; and (iv) OptoFUS constructs with deep quench depths (440) during first cycle, and (v) OptoFUS constructs with deep quench depths (440) during second cycle (442).

Disassembly dynamics of these constructs, upon turning off blue light, has also been tested. As shown in FIG. 10, Without FUS$_N$, Cry2WT (410) only forms noticeable clusters in a small subset of cells, but these disassemble relatively quickly and show no irreversibility even after multiple activation cycles. By contrast, under the same conditions (shallow quench), the optoFUS construct (430) forms clusters which disassemble at a rate roughly 3 fold slower than clusters seen in Cry2WT alone (410); this indicates that the self-associating $FUS_N$ chains interact with sufficient strength to delay dissolution. Gel-like optoFUS clusters assembled from deep quenching (440) also shrink in size upon turning off blue light, while maintaining their overall irregular morphology, and appear to be completely dissolved by ~20 min. Interestingly, despite their reversibility after the first activation cycle, these gel-like clusters disassemble ~1.4 times slower than liquid-like optoFUS droplets (shallow quench) (430), suggesting the material state of clusters impacts the disassembly rate.

When cells expressing optoFUS undergo a sequence of repeated cycles of deep quenching (440), some clusters appear to remain as early as the end of the second cycle (442). By the third cycle, roughly 20% of clusters were not fully dissolved. Concomitantly, the disassembly rate of gel-like clusters gradually slowed down over subsequent cycles. When tested up to five cycles, the number of remaining clusters increases progressively for each cycle. These aggregates are truly irreversible: after the cessation of light activation cycles, they remain assembled for at least 6 hours. Remarkably, no irreversible clustering is observed in liquid-like optoFUS clusters, formed through cycles of shallow quenching (430). One interpretation for these results is that deep quenches develop irreversible aggregates simply because more material has assembled into each cluster. However, even when the total amount of phase separated material is smaller than cells with liquid droplets, cycles through the gel state robustly accumulate irreversible aggregates, confirming that the gel state specifically promotes irreversible aggregate formation.

The gel state provides a crucible for promoting irreversible aggregate formation. This irreversibility is reminiscent of observations of clusters remaining after just a single round of assembly in cells expressing $FUS_N$-Cry2olig. Since $FUS_N$-Cry2olig clusters form gels regardless of quenching depth, prolonged incubation of protein constructs in the gel state due to the slow inactivation rate of Cry2olig may be enough to induce irreversible aggregate formation even from a single round of quenching.

Dynamically tuning protein interactions with light achieves high degree of control over intracellular phase space, which can be exploited to study the phase diagram of FUS-mediated assemblies within living cells. Varying the degree of quenching depth leads to clusters spanning different material states, ranging from liquid droplets to gels. Shallow quenching leads to liquid droplets, similar to those observed with FUS and other proteins both in vitro and in vivo. However, deep quenching results in the formation of gels, which exhibit minimal molecular dynamics and highly irregular aggregate-like morphologies. These assemblies are reminiscent of gel-like structures previously observed in vitro for a variety of globular proteins. Notably, lysozyme, a well-folded protein whose phase behavior has been extensively studied in vitro, exhibits liquid-liquid phase separation at modest supersaturation, but upon deep quenching exhibits phase separation whose progress is arrested, with the condensed material forming a solid-like gel network. The gel state appears to represent a kinetically trapped state arising from the slow relaxation between strongly interacting protein constructs, rather than a thermodynamically favored state. Over time, such gels can develop into crystals and fibers.

This suggests that increasing the strength or effective valency of molecular self-association (e.g., through light activation or endogenously through PTMs) can lead to liquid-liquid phase separation, or for higher supersaturation can result in gelation. It is known that membrane-less organelles can exhibit at least partially solid-like properties (i.e., viscoelasticity). Indeed, large variations in the immobile fraction of stress granule proteins are often measured in FRAP experiments, and in some cases stress granules begin to resemble irregularly shaped gels. These apparent differences in material state reflect different depths into the cytoplasmic phase diagram. This ability to tune material states by moving within the phase diagram could be exploited by cells, since highly dynamic liquid-like states may be useful as microreactors, while gel-like structures would provide an ideal storage environment. However, assembling such arrested, gel-like structures deep within the phase diagram comes with the danger of producing potentially toxic species, due to irreversible aggregation and fibrillization.

Figure 11:
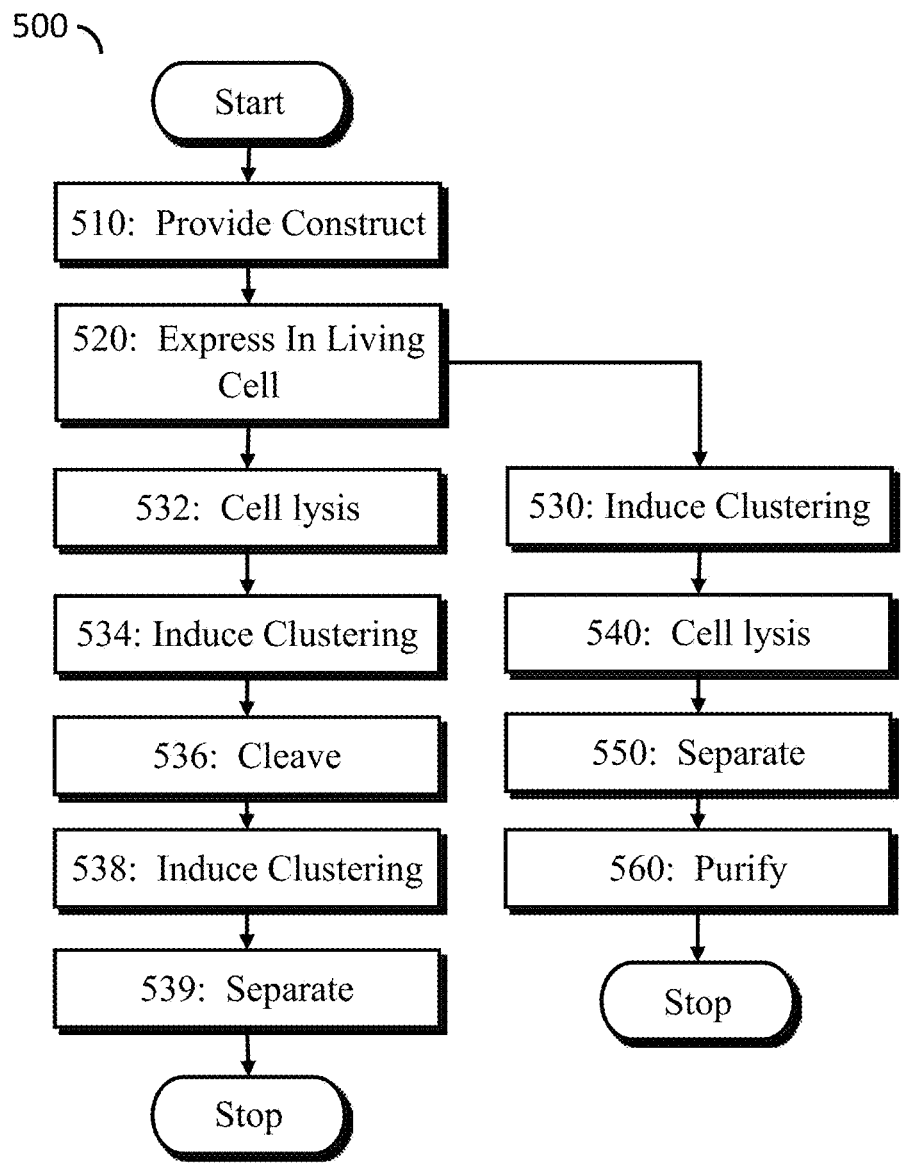
FIG. 11 is a flowchart depicting a method for clustering protein constructs and protein purification.

A method for protein purification, utilizing these constructs, is illustrated in FIG. 11. As described above, the method (500) generally comprises at least seven steps: providing the protein construct (510) as described above, where the protein construct also comprises a target protein (see, e.g., FIG. 1, element 50). The construct is expressed (520) in cells. Cells are then lysed (532) and cellular debris is removed. The induction step (534) is followed by centrifugation to remove molecules other than the clustered protein construct. A cleaving step (536) follows, where the target protein is cleaved from, for example, an intrinsically disordered protein. After cleaving, a second induction step (538) is utilized. The second induction is typically for separating the desired protein to be purified from the remaining portions of the protein constructs. After the second induction step (538), separation (539) can occur, typically via centrifuge.

When a goal is, for example, to purify molecules interacting with the target proteins, the method may be modified slightly. The living cell is exposed to at least one wavelength of light that the proteins sensitive to at least one wavelength of light are responsive to, causing the protein constructs to cluster which inherently induces molecules within the living cell that interact with the target protein_to cluster (530). The induction step can modify at least one of the transport or reactivity of enzymes and other molecules within the living cell, and/or cause intermolecular interactions, protein activation or inactivation, manipulation of signaling pathways, or gene expression through the induction of membrane-less bodies. Cells are gently lysed (540) and the induced clusters are then separated (550), typically via centrifuge, and the separated molecules are then purified (560) using typical protein purification methodologies.

In some embodiments, an induction step may also lead to nucleating droplets of tunable viscoelasticity at defined genomic loci, using at least one of LacO arrays or dCas9. The engineered dCas9 with peptide repeats, for example GCN4 peptide (SEQ ID NO.: 1: EELLSKNYHLENE-VARLKK) or GFP11 (SEQ ID NO.: 2: RDHMVLHEYV-NAAGIT), is co-expressed with a construct comprising the first segment of peptide-binding protein, either scFV-GNC4 or GFP1-10, and the second segment of FUS IDR. Coexpressing sgRNAs programmed for targeting specific genomic loci delivers dCas9 complexes with FUS IDR to the loci, which serves as a seed for droplet assembly. The viscoelasticity of droplets is tuned using the similar strategy described above, a varying degree of supersaturation.

The platform can also facilitate catalytic activity upon photo-stimulation by locally concentrating enzymes inside or outside cells, for instance for intracellular production of natural products, biofuels etc. This may be accomplished by, for example, recruiting enzymes into the phase separated environment generated by the clustering of intrinsically disordered protein regions.

Kits may also be provided to simplify the use of these methods. The kits will generally include a protein construct as described above, as well as at least one light emitting device that can be used to activate the light sensitive proteins of the protein construct.

Thus, specific constructs and methods which can be used for, e.g., rapid and reversible clustering of proteins, have been disclosed. It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A protein construct comprising:
   a first segment comprising at least one protein sensitive to at least one wavelength of light; and
   a second segment fused to the first segment, the second segment comprising an intrinsically disordered protein region (IDR),
   wherein said first segment and said second segment are heterologous.

2. The protein construct according to claim 1, wherein the IDR is at least a portion of FUS.

3. The protein construct according to claim 1, wherein the at least one protein sensitive to at least one wavelength of light is Cry2.

4. The protein construct according to claim 1, wherein the at least one wavelength of light is a visible wavelength of light between and including 400 and 800 nm.

5. The protein construct according to claim 1, wherein the IDR is at least a portion of FUS, the at least one protein sensitive to at least one wavelength of light is Cry2, and the N-terminal IDR of FUS is fused to a photolyase homology region of Cry2.

6. The protein construct according to claim 1, further comprising at least one fluorophore fused between the first segment and the second segment.

7. The protein construct according to claim 6, wherein the fluorophore is mCherry.

8. The protein construct according to claim 6, wherein the IDR is at least a portion of FUS, the at least one protein sensitive to at least one wavelength of light is Cry2, and wherein the IDR is fused to a mCherry-labeled Cry2 photolyase homology region.

9. The protein construct according to claim 1, wherein the IDR is at least a portion of Ddx4.

10. The protein construct according to claim 1, wherein the IDR is at least a portion of hnRNPA1.

11. The protein construct according to claim 1, wherein the second segment further comprises at least one fluorophore fused to the at least one protein sensitive to at least one wavelength of light.

12. A method for clustering protein constructs, comprising the steps of:
   i) providing a protein construct comprising:
      a first segment comprising at least one protein sensitive to at least one wavelength of light;
      a second segment fused to the first segment, the second segment comprising an intrinsically disordered protein region (IDR), and
      a third segment comprising at least one target protein to be purified,
      wherein seed first, second, and the third segments are heterologous,
   ii) introducing the protein construct into a living cell; and
   iii) inducing the protein construct within the living cell to cluster by exposing the protein construct to at least one predetermined wavelength of light at a predetermined intensity for a predetermined period of time,
      wherein the protein constructs cluster in response to the light.

13. The method according to claim 12, wherein inducing the protein construct to cluster modifies at least one of the transport or reactivity of molecules within the living cell.

14. The method according to claim 12, wherein inducing the protein construct to cluster causes intermolecular interactions, protein activation or inactivation, manipulation of signaling pathways, or gene expression through the induction of membrane-less bodies.

15. The method according to claim 12, further comprising the steps of:
   separating the protein construct via centrifuge.

16. The method according to claim 12, wherein the protein construct further comprises a cleavage tag fused between the second segment and the third segment.

17. The method according to claim 16, wherein the cleavage tag is selected from the group consisting of: Human Rhinovirus 3C Protease (3C/PreScission), Enterokinase (EKT), Factor Xa (FXa), Tobacco Etch Virus Protease (TEV), and Thrombin (Thr).

18. The method according to claim 16, wherein the cleavage tag is a self cleaving tag.

19. The method according to claim 16, further comprising the steps of:
   cleaving the target protein from the protein construct; and
   exposing the at least one protein sensitive to at least one wavelength of light to the at least one predetermined wavelength of light.

20. A kit for inducing in vivo aggregation or liquid-liquid phase separation, comprising:
   one or more aliquots of composition comprising: a protein construct comprising:
   a first segment comprising at least one protein sensitive to at least one wavelength of light; and
   a second segment fused to the first segment, the second segment comprising an intrinsically disordered protein region (IDR),
   wherein said first segment and said second segment are heterologous, and
   at least one light emitting device configured to activate at least a portion of the protein construct.

* * * * *